(12) United States Patent
Knox et al.

(10) Patent No.: US 10,399,292 B2
(45) Date of Patent: Sep. 3, 2019

(54) HIGH NUMERICAL APERTURE OPTOMECHANICAL SCANNER FOR LAYERED GRADIENT INDEX MICROLENSES, METHODS, AND APPLICATIONS

(71) Applicant: University of Rochester, Rochester, NY (US)

(72) Inventors: Wayne H. Knox, Pittsford, NY (US); Jonathan Ellis, Pittsford, NY (US)

(73) Assignee: University of Rochester, Rochester, NY (US)

( * ) Notice: Subject to any disclaimer, the term of this patent is extended or adjusted under 35 U.S.C. 154(b) by 784 days.

(21) Appl. No.: 14/903,165

(22) PCT Filed: Jul. 8, 2014

(86) PCT No.: PCT/US2014/045668
§ 371 (c)(1),
(2) Date: Jan. 6, 2016

(87) PCT Pub. No.: WO2015/006274
PCT Pub. Date: Jan. 15, 2015

(65) Prior Publication Data
US 2016/0144580 A1     May 26, 2016

Related U.S. Application Data

(60) Provisional application No. 61/843,553, filed on Jul. 8, 2013.

(51) Int. Cl.
*A61F 9/008*     (2006.01)
*B23K 26/082*   (2014.01)
(Continued)

(52) U.S. Cl.
CPC .... *B29D 11/00355* (2013.01); *A61F 9/00825* (2013.01); *A61F 9/00827* (2013.01);
(Continued)

(58) Field of Classification Search
CPC ......... B29D 11/00355; B29D 11/00461; A61F 9/00827; A61F 9/00842; A61F 2/14;
(Continued)

(56) References Cited

U.S. PATENT DOCUMENTS 6,181,474 B1    1/2001   Ouderkirk et al.
2007/0097340 A1  5/2007   Yuan et al.
(Continued)

FOREIGN PATENT DOCUMENTS

WO    WO-2013044388 A1    4/2013
WO    WO-2013082247 A1    6/2013

OTHER PUBLICATIONS

United States Patent and Trademark Office—International Search Report and Written Opinion of the International Searching Authority for International Application No. PCT/US2014/045668 dated Oct. 31, 2014 (10 pages).

(Continued)

*Primary Examiner* — Boniface N Nganga
(74) *Attorney, Agent, or Firm* — Harris Beach PLLC

(57) ABSTRACT

A high numerical aperture opto-mechanical scanner for writing refractive index modifications includes a fast axis scanner having a fast scanning axis. A waveform generator is electrically coupled to the fast axis scanner, and a waveform is provided by the waveform generator which defines a fast scan of the fast axis scanner. A scanning lens assembly is mechanically coupled to the fast axis scanner, the scanning lens assembly having a NA greater than 0.5 and a scanning lens motion along the fast scanning axis. A femtosecond laser is optically coupled through the scanning lens (Continued)

assembly to a surface of a material, creating a femtosecond laser light scanning pattern to write the refractive index modifications into the material. A method for writing refractive index modifications using a high numerical aperture opto-mechanical scanner is also described.

27 Claims, 33 Drawing Sheets

(51) Int. Cl.
    *G02B 26/10*     (2006.01)
    *B29D 11/00*     (2006.01)
    *B23K 26/0622*     (2014.01)
    *B29K 105/00*     (2006.01)

(52) U.S. Cl.
    CPC ........ *B23K 26/0624* (2015.10); *B23K 26/082* (2015.10); *B29D 11/00461* (2013.01); *G02B 26/10* (2013.01); *A61F 2009/00842* (2013.01); *A61F 2009/00872* (2013.01); *B29K 2105/0061* (2013.01)

(58) Field of Classification Search
    CPC ...... A61F 2/16; A61F 2/1627; A61F 9/00825; A61F 2009/00827; A61F 2009/00842; B23K 26/0624; B23K 26/082; G02B 26/10; A61L 2430/16; A61L 27/50
    See application file for complete search history.

(56) References Cited

U.S. PATENT DOCUMENTS

2009/0287306 A1    11/2009    Smith et al.
2012/0310340 A1    12/2012    Knox et al.

OTHER PUBLICATIONS

Ding, Li et al., "Large refractive index change in silicone-based and non-silicone-based hydrogel polymers induced by femtosecond laser micro-machining," 2006 Optics Express, vol. 14, No. 24 (pp. 11901-11909).
Ding, Li et al., "Intratissue Refractive Index Shaping (IRIS) of the Cornea and Lens Using a Low-Pulse-Energy Femtosecond Laser Oscillator," 2008 Investigative Ophthalmology & Visual Science, vol. 49, No. 12 (pp. 5332-5339).
Xu, Lisen et al., "Lateral gradient index microlenses written in ophthalmic hydrogel polymers by femtosecond laser micromachining," 2011 Optical Materials Express, vol. 1, No. 8 (pp. 1416-1424).
Ellis, Jonathan D. et al., "Fiber-Coupled 3-DOF Interferometer for EUV Lithography Stage Metrology," 2012 Proceedings of ASPE Summer Topical Meeting: Amercian Society for Precision Engineering, vol. 53 (pp. 36-41).
Gillmer, Steven et al., Miniature, Fiber-Coupled 3-DOF Interferometer for Precision Micro-Motion Stage Metrology, 2012 Proceedings of the 27th ASPE Annual Meeting, vol. 54 (pp. 77-80).
Kashiwagei Masahiro et al., "Effectively single-mode all-solid photonic bandgap fiber with large effective area and low bending loss for compact high-power all-fiber lasers," 2012 Optics Express, vol. 20, No. 14 (pp. 15061-15070).
Wang, Lidai et al., "Fast voice-coil scanning optical-resolution photoacoustic microscopy," 2011 Optics Letters, vol. 36, No. 2 (pp. 139-141).
Minoshima, Kaoru et al., "Photonic device fabrication in glass by use of nonlinear materials processing with a femtosecond laser oscillator," 2001 Optics Letters, vol. 26, No. 19 (pp. 1516-1518).
Minoshima, Kaoru et al., "Fabrication of coupled mode photonic devices in glass by nonlinear femtosecond laser materials processing," 2002 Optics Express, vol. 10, No. 15 (pp. 645-652).
Davis, K.M. et al., "Writing waveguides in glass with a femtosecond laser," 1996 Optics Letters, vol. 21, No. 21 (pp. 1729-1731).
Takeshima, Nobuhito et al., Fabrication of a periodic structure with a high refractive-index difference by femtosecond laser pulses, 2004 Optics Express, vol. 12, No. 17 (pp. 4019-4024.
Takeshima, Nobuhito et al., "Fabrication of high-efficiency diffraction gratings in glass," 2005 Optics Letters, vol. 30, No. 4 (pp. 352-354).
Osellame, Roberto et al., "Optical waveguide writing with a diode-pumped femtosecond oscillator," 2004 Optics Letters, vol. 29, No. 16 (pp. 1900-1902).
Schaffer, Chris B. et al., "Micromachining bulk glass by use of femtosecond laser pulses with nanojoule energy," 2001 Optics Letters, vol. 26, No. 2 (pp. 93-95).
Streltsov, Alexander M. et al., Fabrication and analysis of a directional coupler written in glass by nanojoule femtosecond laser pulses, 2001 Optics Letters, vol. 26, No. 1 (pp. 42-43).
Streltsov, Alexander M. et al., "Study of femtosecond-laser-written waveguides in glasses," 2002 J. Opt. Soc. Am. B, vol. 19, No. 10 (pp. 2496-2504).
Glezer, E.N. et al, "3-D Optical Storage Inside Transparent Materials," 1996 Optics Letters, vol. 21, No. 24 (pp. 2023-2025).
Nasu, Yusuke et al., "Low-loss waveguides written with a femtosecond laser for flexible interconnection in a planar light-wave circuit," 2005 Optics Letters, vol. 30, No. 7 (pp. 723-725).
Xu, Lisen, "Femtosecond Laser Processing of Ophthalmic Materials and Ocular Tissues: A Novel Approach for Non-invasive Vision Correction," 2013 Thesis: University of Rochester, Rochester, NY (344 pages).
Ding, Li et al., "Large enhancement of femtosecond laser micromachining speed in dye-doped hydrogel polymers," 2008 Optics Express, vol. 16, No. 26 (pp. 21914-21921).
Nagy, Lana J. et al., "Potentiation of Femtosecond Laser Intratissue Refractive Index Shaping (IRIS) in the Living Cornea with Sodium Fluorescein," 2010 Investigative Ophthalmology & Visual Science, vol. 51, No. 2, (pp. 850-856).
Xu, Lisen et al., "Noninvasive Intratissue Refractive Index Shaping (IRIS) of the Cornea with Blue Femtosecond Laser Light," 2011 Investigative Ophthalmology & Visual Science, vol. 52, No. 11 (pp. 8148-8155).
Brooks, Daniel R. et al., "Precision High Numerical Aperture Scanning System for Femtosecond Micromachining of Ophthalmic Materials Over Large Field," 2013 Proceedings of the 27th ASPE Annual Meeting, American Society for Precision Engineering, vol. 56 (pp. 58-62).
Wang, Chen, "FPGA-based, 4-channel, High-speed Phasemeter for Heterodyne Interferometry," 2013 Thesis, University of Rochester, Rochester, NY (153 pages).
Ellis, Jonathan D. et al., "Fiber-Coupled 3-DOF Interferometer for EUR Lithography Stage Metrology," 2012 Proceedings of ASPE Summer Topical Meeting, American Society for Precision Engineering, vol. 53 (pp. 36-41).
Gillmer, Steven et al., "Miniature, Fiber-Coupled 3-DOF Interferometer for Precision Micro-Motion Stage Metrology," 2012 Proceedings of the 27th ASPE Annual Meeting, American Society for Precision Engineering, vol. 54 (pp. 77-80).

NEGATIVE LENS WITH INTENSITY CONTROL IN SHAKER &
SCAN DIRECTIONS TO GENERATE COMPLEX REFRACTIVE STRUCTURE

POSITIVE LENS WITH INTENSITY CONTROL IN SHAKER &
SCAN DIRECTIONS TO GENERATE COMPLEX REFRACTIVE STRUCTURE

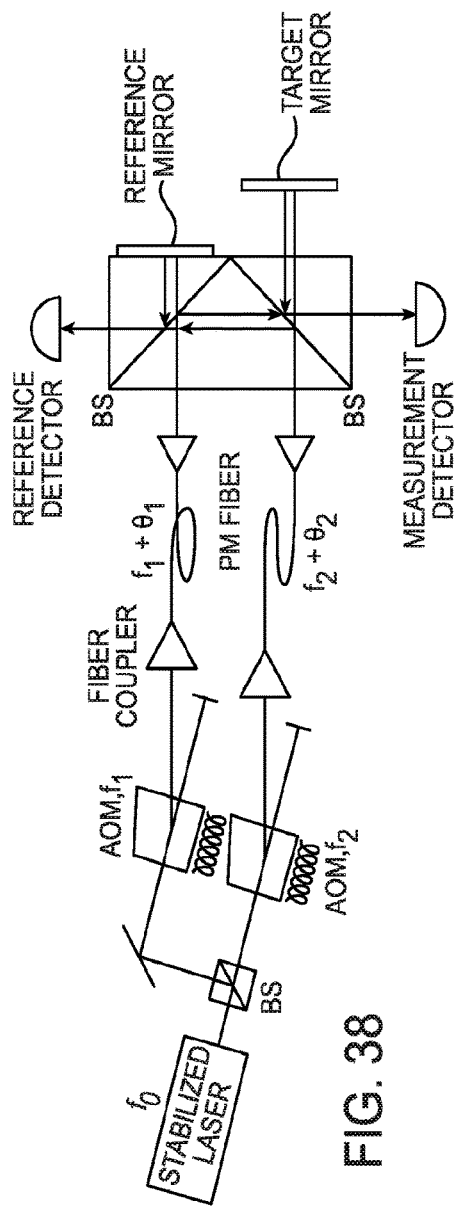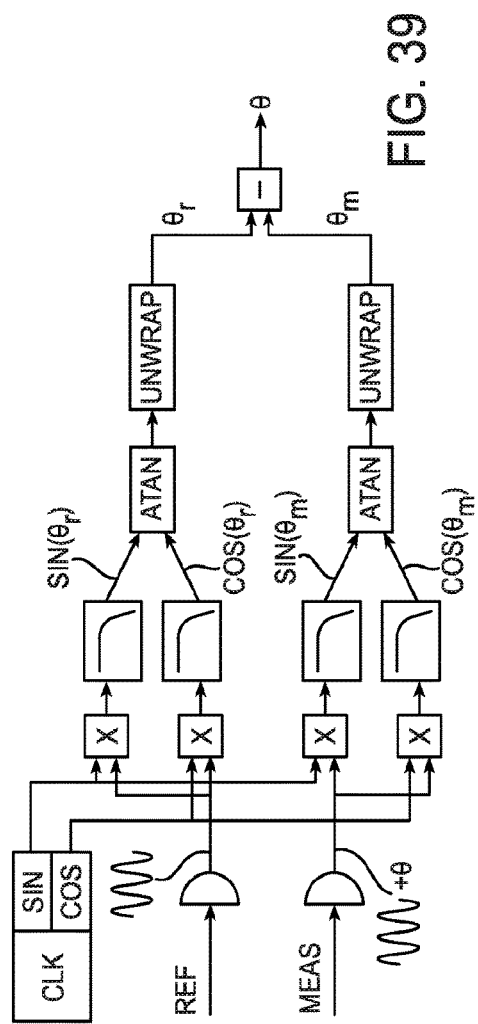

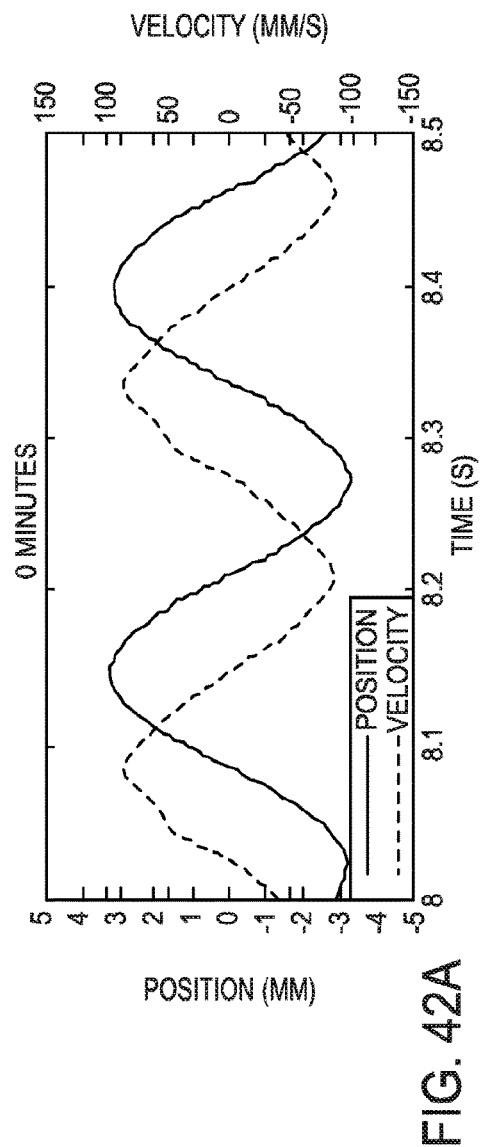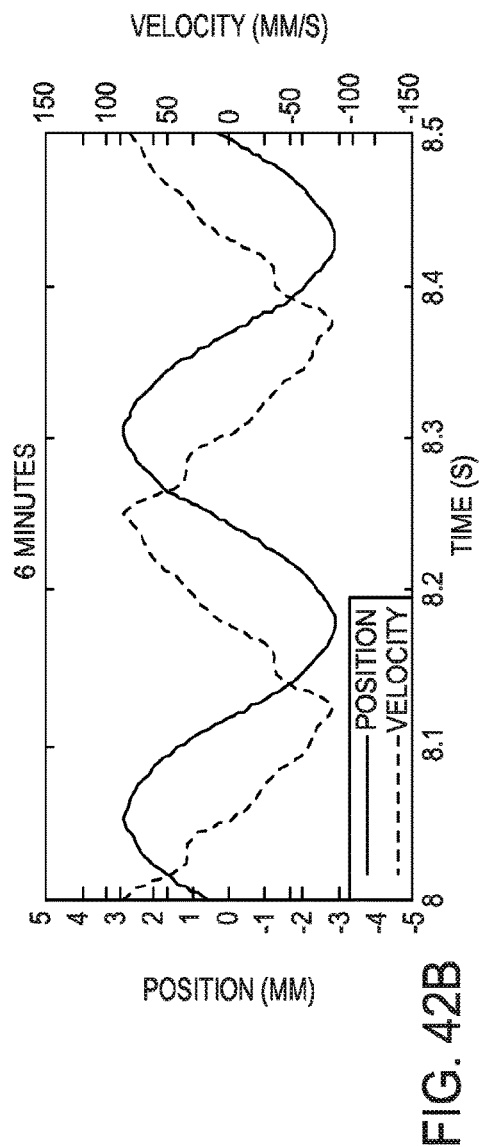
FIG. 42A
FIG. 42B

HIGH NUMERICAL APERTURE OPTOMECHANICAL SCANNER FOR LAYERED GRADIENT INDEX MICROLENSES, METHODS, AND APPLICATIONS

CROSS-REFERENCE TO RELATED APPLICATIONS

This application is a national stage application under 35 U.S.C. § 371 of PCT Application No. PCT/US2014/045668, filed Jul. 8, 2014, HIGH NUMERICAL APERTURE OPTO-MECHANICAL SCANNER FOR LAYERED GRADIENT INDEX MICROLENSES, METHODS AND APPLICATIONS which claims priority to and the benefit of U.S. provisional patent application Ser. No. 61/843,553, HIGH NUMERICAL APERTURE OPTOMECHANICAL SCANNER FOR LAYERED GRADIENT INDEX MICROLENSES, METHODS AND APPLICATIONS, filed Jul. 8, 2013, which applications are incorporated herein by reference in their entirety.

STATEMENT REGARDING FEDERALLY FUNDED RESEARCH OR DEVELOPMENT

This invention was made with government support under award no. 70NANB12H186 awarded by U.S. Department of Commerce, National Institute of Standards and Technology. The government has certain rights in the invention.

FIELD OF THE APPLICATION

The application relates to writing refractive indexes into a medium, and particularly to writing refractive index changes into a material to create or modify a lens structure.

BACKGROUND

In the background, other than the bolded paragraph numbers, non-bolded square brackets ("[ ]") refer to the citations listed hereinbelow.

In the field of high resolution imaging, laser scanning microscopes have been developed to provide high resolution (nearly diffraction-limited) to achieve very fine resolution pictures over a small field of view (typically a few hundred micrometers at a time) through a variety of modalities such as fluorescence mode imaging, differential interference contrast, or phase-contrast imaging. The use of galvanometer scanning mirrors allows such systems to reposition rapidly and draw nearly arbitrary patterns, however generally the use of such galvanometers with high numerical aperture (NA) microscope objectives results in small field sizes, because the field size is the effective focal length times the tangent of the maximum full field angle allowed by the microscope objective.

Traditionally, optical structures with refracting power, such as lenses, are made of a material where the refractive index (RI) and curvature of the surfaces determine the amount of refracting power [9]. For example, in ophthalmic applications, different curvatures and higher order shapes can be used to generate desired prescriptions in devices such as eyeglasses, contact lenses, and intraocular lenses, with materials such as glasses and plastics with different index of refraction.

SUMMARY

According to one aspect, a high numerical aperture opto-mechanical scanner for writing refractive index modifications includes a fast axis scanner having a fast scanning axis. A waveform generator is electrically coupled to the fast axis scanner, and a waveform is provided by the waveform generator which substantially defines a fast scan motion profile of the fast axis scanner. A scanning lens assembly is mechanically coupled to the fast axis scanner, the scanning lens assembly has a NA greater than about 0.5 and a scanning lens motion along the fast scanning axis. A femtosecond laser is optically coupled through the scanning lens assembly to a surface of a material, creating a femtosecond laser light scanning pattern to write the refractive index modifications into the material.

In one embodiment, the material includes a cornea of an animal or human eye.

In another embodiment, the material includes a hydrogel.

In yet another embodiment, the waveform includes an arbitrary waveform or a sine wave.

In yet another embodiment, the high numerical aperture opto-mechanical further includes a modulator disposed between the laser and the material.

In yet another embodiment, the fast axis scanner further includes a balancing mass that substantially matches a scanning lens assembly mass.

In yet another embodiment, the fast axis scanner and the scanning lens assembly is mounted on a slow scanning stage having a slow scan motion axis substantially orthogonal to the fast scanning axis.

In yet another embodiment, the high numerical aperture opto-mechanical scanner further includes a rotation stage.

In yet another embodiment, the high numerical aperture opto-mechanical scanner further includes a z-axis scanner having an axis substantially orthogonal to both the fast scanning axis and the slow scan motion axis.

In yet another embodiment, the scanning lens assembly includes a depth control stage or a spherical aberration correction stage.

In yet another embodiment, the high numerical aperture opto-mechanical scanner includes an optical sensor that provides a measurement selected from the group consisting of displacement, straightness, pitch, yaw and roll of the scanning lens assembly to correct a position of the scanning lens assembly during scanning.

In yet another embodiment, the high numerical aperture opto-mechanical scanner further includes a fiber coupling lens and an optical fiber disposed between the femtosecond laser and the scanning lens assembly.

According to another aspect, a method for writing refractive index modifications using a high numerical aperture opto-mechanical scanner includes the steps of; providing a fast axis scanner having an optical assembly with a NA greater than about 0.5, a fast scanning motion axis of the optical assembly controlled by a waveform generator, a second motion axis orthogonal to the fast scanning motion axis, and a femtosecond laser to write the refractive index modifications; providing a working surface including a surface of an optical material or a live animal or human eye; and writing by movement of the optical assembly along the fast scanning motion axis and the second motion axis at least a two dimensional refractive index modification of the material.

In one embodiment, the step of providing further includes providing a third motion axis orthogonal to both of the fast scanning axis and the second motion axis, and the step of writing includes writing a three dimensional refractive index modification of the material.

In another embodiment, the step of providing further includes providing an optical modulator disposed between the femtosecond laser and the working surface, and the step of writing further includes writing a three dimensional refractive index modification modulated by the optical modulator.

In yet another embodiment, the step of providing further includes providing an optical modulator disposed between the femtosecond laser and the working surface or the second motion axis controlled by a stepping motion, and the step of writing includes writing a microlens with a parabolic phase profile by use of intensity or speed control.

In yet another embodiment, the step of writing includes writing an accumulated phase structure in modulo-$2\pi$.

In yet another embodiment, the step of providing further includes providing an arbitrary waveform generator to control the fast scanning motion axis and the step of writing includes writing a changing index profile controlled by a waveform of the arbitrary waveform generator along lines of the fast scanning motion axis.

In yet another embodiment, the step of providing the waveform generator includes providing a sine wave generator and the step of writing includes writing a negative refractive index lens.

In yet another embodiment, the step of writing includes writing a positive refractive index lens using a two-scan process wherein each scan process of the two-scan process writes half a profile block.

In yet another embodiment, the step of writing includes writing one or more arbitrary negative lenses or arbitrary positive lenses The foregoing aspects, features, and advantages of the invention will become more apparent from the following description and from the claims.

BRIEF DESCRIPTION OF THE DRAWINGS

The features of the application can be better understood with reference to the drawings described below, and the claims. The drawings are not necessarily to scale, emphasis instead generally being placed upon illustrating the principles of the application. In the drawings, like numerals are used to indicate like parts throughout the various views.

FIG. 38 shows a schematic of an exemplary interferometer;

FIG. 39 shows a block diagram of an exemplary process algorithm used to analyze the signal received from the interferometer;

FIG. 42A shows a graph of position and velocity versus time at 0 minutes;

FIG. 42B shows a graph of position and velocity versus time at 6 minutes;

DETAILED DESCRIPTION

Figure 1:
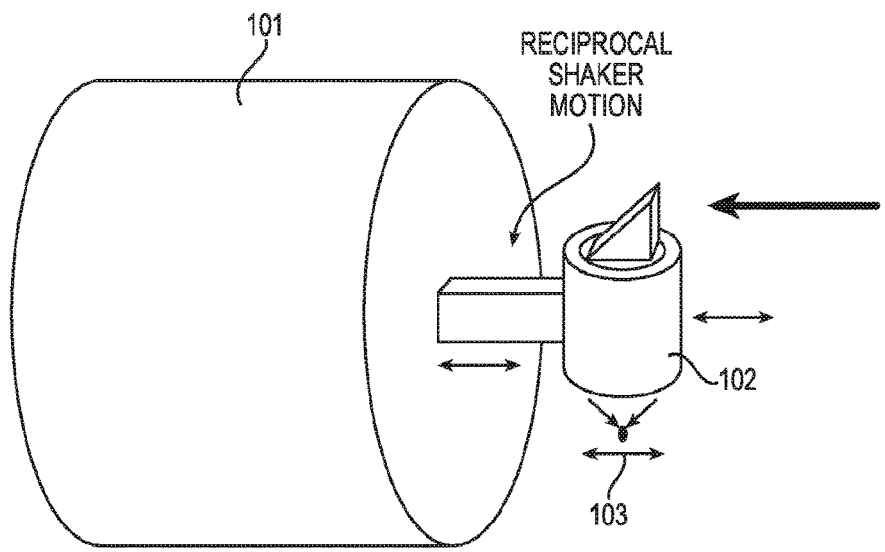
FIG. 1 shows an illustration of a first exemplary embodiment of a high numerical aperture optomechanical scanner.

In the description, other than the bolded paragraph numbers, non-bolded square brackets ("[ ]") refer to the citations listed hereinbelow.

Definitions

Waveform generator includes any suitable generator that provides a waveform. The waveform generator can be, such as for prototyping and experimentation, a commercially available arbitrary waveform generator, function generator, or any other suitable waveform generator, such as, for example, those commercially available from the Agilent Technologies™ Corporation of Santa Clara, Calif. Production equipment using the new systems and methods described hereinbelow can use any suitable waveform generator as known in the art including, for example, one or more dedicated digital and/or analog electronic circuits embedded within the apparatus. That is, there need not be a present a distinct waveform generator apparatus. The waveform, typically an electrical waveform, can be translated by an actuator such as, for example, a motor or stepping motor, into a mechanical motion along a mechanical axis. Some types of actuators may include a controller that accepts a waveform from the waveform generator and converts it into one or more control signals suited to a particular type of actuator. It is unimportant whether the waveform is an analog or digital electrical waveform or, analog or digital optical waveform (e.g. when transmitting the waveform via a fiber optic cable).

Modulator:

A modulator as used hereinbelow is typically an optical modulator disposed in an optical path between a laser used to write a refractive index modification into a material, and a surface of the material. The modulator can be an electro-optic modulator, an acousto-optic modulator, or any other suitable type of modulator for adjusting the power of the laser.

Computer:

It is understood that most embodiments of the new systems and methods described hereinbelow will operate under the control of one or more computers. Any suitable type of computer can be used. For example, embodiments for prototyping can be controlled by a desktop computer, laptop computer, workstation, etc. Production apparatus performing the new methods described hereinbelow are more likely to include one or more embedded computers, such as, for example, one or more microcomputers, microprocessors, microcontrollers, or any other suitable digital circuitry (e.g. field programmable gate arrays (FPGA) or equivalent programmed to perform the functionality of a microprocessor, microcontroller, microcomputer, etc. Some of the exemplary embodiments described hereinbelow were controlled by and/or performed data acquisition and/or data analysis using software such as MATLAB™ available from Mathworks™ of Natick, Mass.

As described hereinabove, in the field of laser scanning systems, there are many examples of using flying-spot systems such as supermarket checkout scanners, laser display scanners, and laser beam scanners for industrial cutting or welding of materials. In those systems, large areas can be scanned without the need to focus the laser beam to a tiny spot.

In the field of high resolution imaging, laser scanning microscopes have been developed to provide high resolution (nearly diffraction-limited) to achieve very fine resolution pictures over a small field of view (typically a few hundred micrometers at a time) through a variety of modalities such as fluorescence mode imaging, differential interference contrast, or phase-contrast imaging. The use of galvanometer scanning mirrors allows such systems to reposition rapidly and draw nearly arbitrary patterns, however generally the use of such galvanometers with high numerical aperture (NA) microscope objectives results in small field sizes, because the field size is roughly the effective focal length times the maximum full field angle allowed by the microscope objective.

For a typical NA/0.7 microscope objective, the effective focal length is only 2 mm, resulting in a roughly 300 micrometer full field scanning area. This is fine for microscopy, however for some applications it is required to scan a much larger area while maintaining high numerical aperture. For vision correction applications in particular, devices are written at up to 6 mm diameter, or larger.

Recently we developed a technology for writing refractive index modifications in a working surface of a range of materials that are of interest for ophthalmic applications, including hydrogels [1], cornea [2]. Writing of lateral gradient index microlenses was also demonstrated [3] using a technique of holding the focusing lens stationary while moving the sample. In that case, there is no limitation to how large a scan area can be covered, limited only by the scanning stage characteristics.

As described hereinbelow more detail, we realized that a scanning lens can be mounted directly onto a rapidly moving industrial vibration testing impeller that is driven with an arbitrary waveform generator. By making use of the previously measured calibrations of index change as a function of laser power, wavelength and scan speed, we can now write millimeter-scale devices (up to about 8 mm wide) at speeds exceeding 100 mm/sec.

FIG. 1 shows an illustration of a first exemplary embodiment of a high numerical aperture (e.g. NA>about 0.5) optomechanical scanner having a reciprocal shaker (e.g. a rapidly shaking impeller) as a fast axis scanner 101 which causes a fast motion along a fast scanning motion axis of a microscope objective as an optics assembly 102 (also called hereinbelow a scanning lens assembly or optical assembly) having a scanning lens motion along the fast scanning axis 103. In the embodiment of FIG. 1 as well as later embodiments, the focused spot follows the scan pattern of the lens. The fast motion provides a rapidly scanning (up to 100 Hz, in principle for the exemplary embodiment of FIG. 1) and a focus spot at up to about ±3 mm range (fast axis; about ±4.4 mm to obtain about ±3 mm in clean pattern) in the present implementation, without limiting the NA of the objective.

Compared to galvanometer scanning implementations, the new high numerical aperture optomechanical scanner, such as shown in FIG. 1, and related embodiments described hereinbelow are superior for the intended applications because the Strehl Ratio (the ratio of power contained in the main central lobe divided by the total power) is maintained near unity over the whole scan range. In galvanometer scanners, the Strehl Ratio necessarily drops off near the scan edges as a result of uncorrected high order aberrations such as coma and astigmatism.

Maintaining a nearly constant Strehl Ratio is important for maintaining calibrated index of refraction writings. In this embodiment of FIG. 1 as well as in later embodiments, the input beam is carefully aligned with the shaking axis so that it maintains alignment. Maintaining such alignment can be accomplished, for example, by mounting a right angle prism on the input face of the microscope objective, but could also be done by any other suitable technique, such as, for example with a small mirror that is rigidly mounted.

Figure 2:
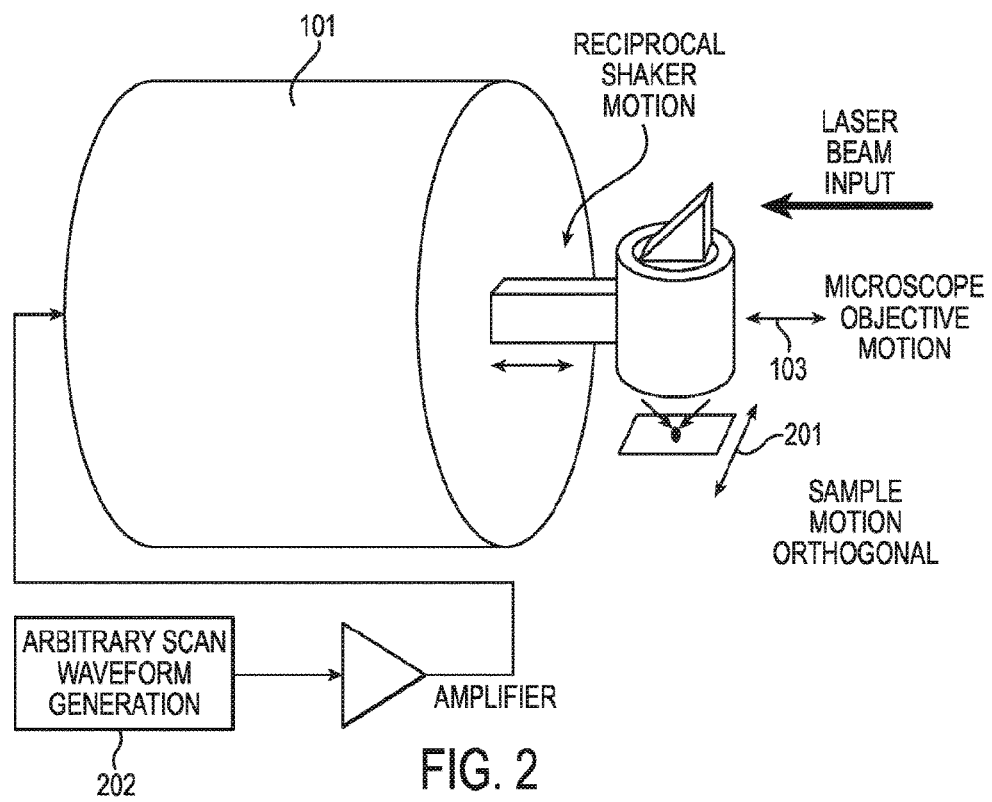
FIG. 2 shows an illustration of a first exemplary embodiment of a high numerical aperture optomechanical scanner having a second sample motion axis.

FIG. 2 shows an illustration of a first exemplary embodiment of a high numerical aperture optomechanical scanner having a second sample motion axis 201 (a slow scan motion axis) orthogonal to the fast scanning axis 103. In order to write a lateral gradient index lens, the sample can be mounted to a stepping motor stage that steps orthogonally to the fast shaking axis (e.g. fast scanning axis 103). Using such techniques, a lateral gradient index microlens can be written by changing the scanning speed after each line is written, and/or by changing the laser intensity before the next line is written. In the exemplary embodiment of FIG. 2, the fast scanning axis 103 of the reciprocal scanner is controlled by an Arbitrary Waveform Generator 202. The waveform for the fast axis is calculated in order to result in the desired refractive index pattern along the fast axis. The samples can be mounted on a rotation stage for flexibility in orienting the fast scanning direction.

Figure 3:
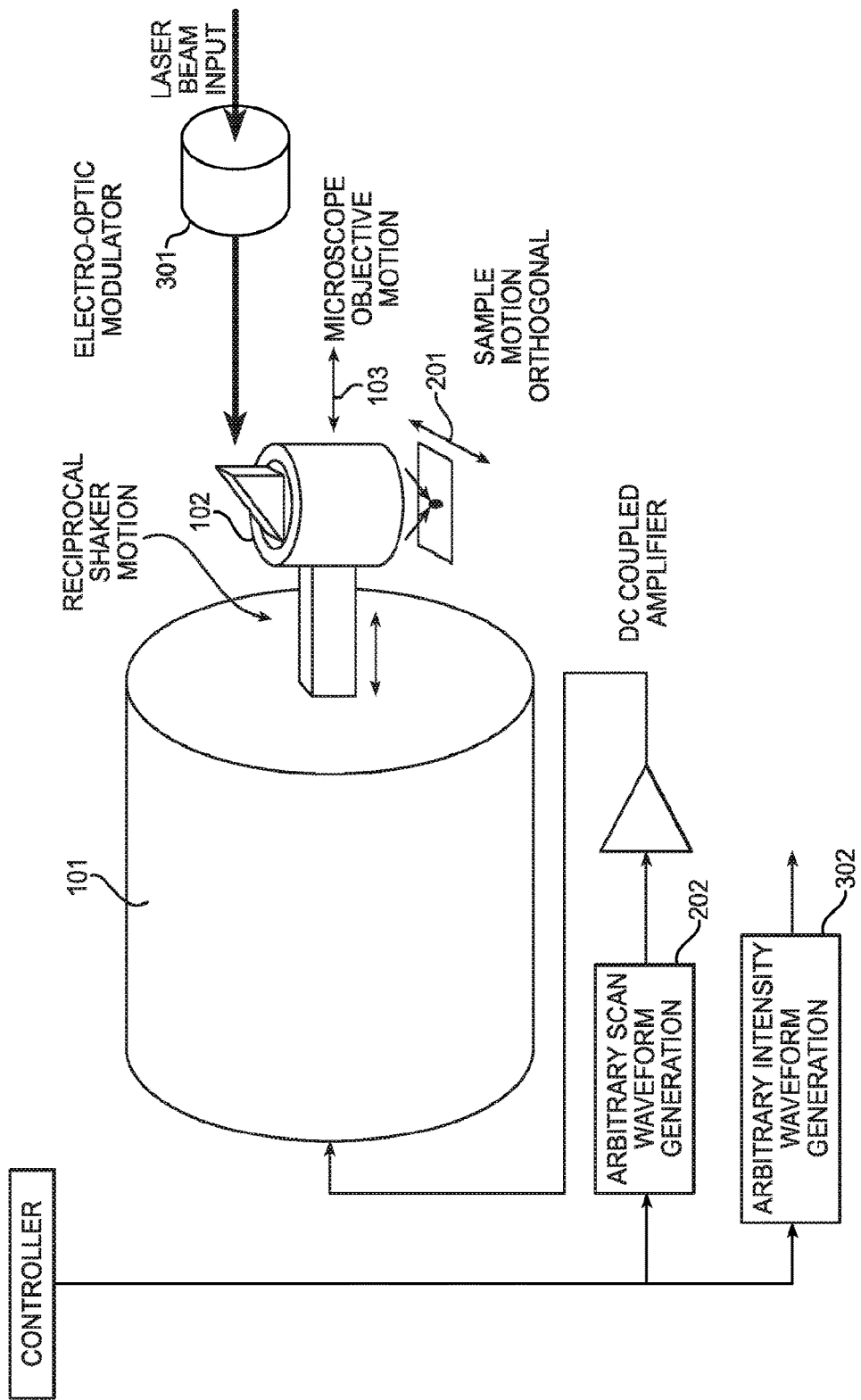
FIG. 3 shows an illustration of a first exemplary embodiment of a high numerical aperture optomechanical scanner having an electro-optic modulator.

FIG. 3 shows an illustration of a first exemplary embodiment of a high numerical aperture optomechanical scanner having an optical modulator, such as, for example, an electro-optic modulator 301. The fast scanner is controlled by an arbitrary waveform generator 202, and the laser intensity is controlled by a second synchronized arbitrary waveform generator 302. The laser intensity can be controlled by the use of an electro-optic modulator 301 or acousto-optic modulator (not shown in FIG. 3) so that the intensity can be changed while the fast scan is proceeding, or the intensity could be reset to a new fixed value before each new line is written. And, in fact both can be done so that a fully customized refractive correction could be written by full control of the intensity and the scan velocity. The embodiment of FIG. 3 is an exemplary arrangement that would allow for such full customization.

Instead of sending an arbitrary waveform to the shaker stage, a sine wave (e.g. a sine wave from an arbitrary waveform generator, or from sine wave generator) tuned to the design specifications can be sent instead to maximize the performance. The shaker stage includes of a mass (holding the microscope objective) and springs. The drive frequency can be tuned similar to a jackhammer, such that it takes a relatively small input force to drive the stage near its resonance frequency. This will enable a long stroke, high speed motion while inducing minimal disturbances into the base, but will not completely eliminate them.

Figure 4:
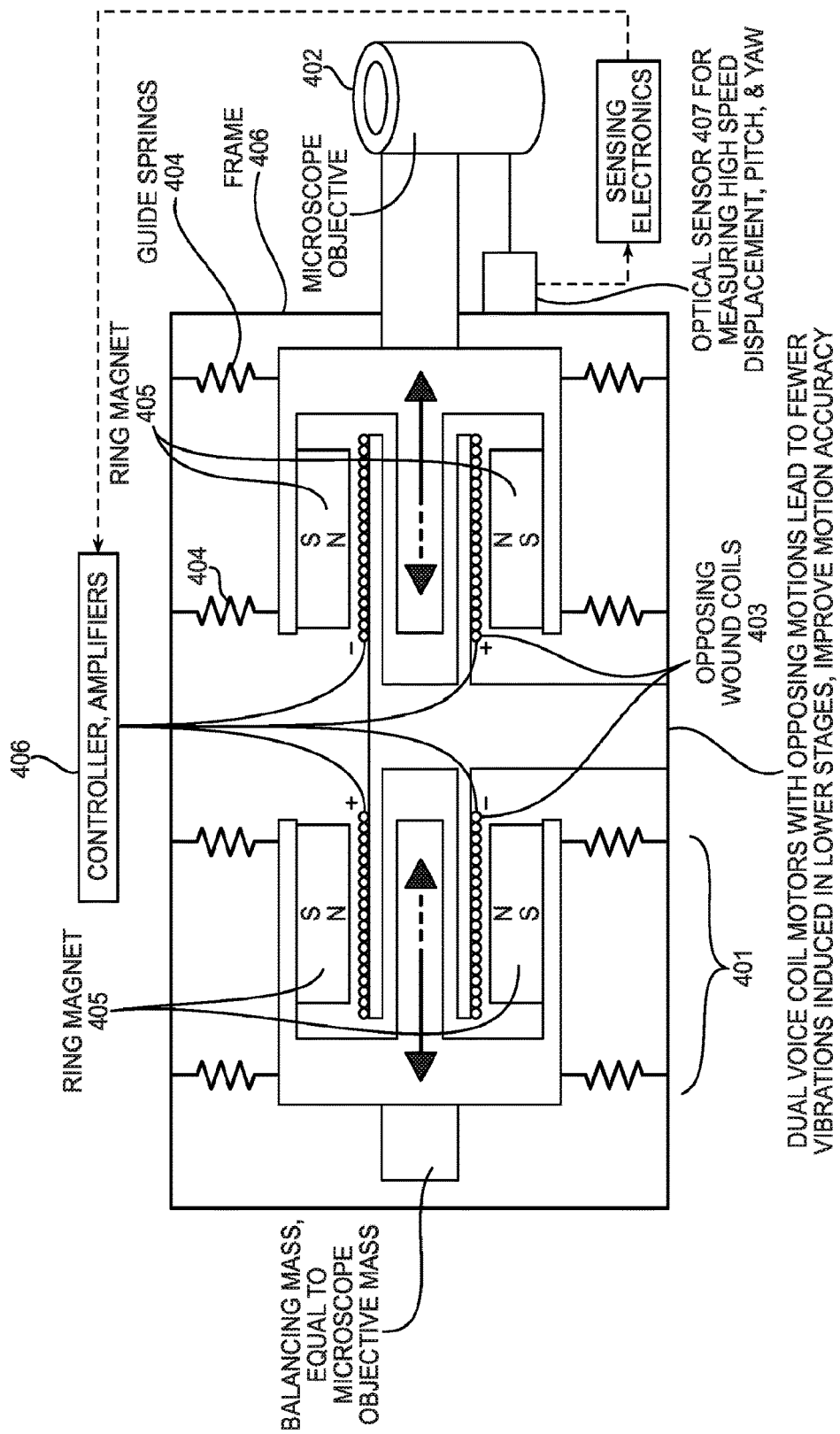
FIG. 4 shows an exemplary dual voice coil drive system to reduce vibrations induced in the base.

FIG. 4 shows an exemplary dual voice coil drive system to reduce vibrations induced in the base. The drive frequency can be tuned based on the moving mass and guide springs 404 to ensure that a long stroke and high speed stage positioning can be achieved. The second stage 401 can be employed with a balancing mass equal to the microscope objective 402 mass (i.e. the scanning lens assembly mass of the fast axis scanner mass) to further reduce vibrations into the base, as shown in FIG. 4. By connecting both coils 403 and wiring them with opposite polarity, the net force on the shaker base and frame can be minimized, improving the accuracy, specifically when this shaker stage is used in conjunction with a series of stacked stages for 3 degree-of-freedom positioning. The shaker stage is typically based on a linear voice coil (section view in FIG. 4), having a ring magnet 405, ferromagnetic support structure 406, coil windings 403, and support guide springs 404. In some embodiments, the ring magnet 405 or coil windings 403 can be placed on the support guide springs 404 with the other mounted directly to the second stage 401.

The position of the microscope objective can be measured relative to the frame/base (using e.g. [4,5]) such as by an optical sensor 407, such as, for example, for measuring high speed, displacement, pitch & yaw, and then its position can be set to a controller and amplifier 406 to ensure the microscope is being accurately positioned. If a secondary metrology frame (not shown) is used, then the microscope objective can also be measured relative to that fixed metrology frame.

In the implementations shown in FIGS. 2 and 3 the sample is translated along the slow axis. In some cases such as in surgical procedures where a refractive index change is written to a surface of a live animal eye or a human eye of a live animal or human patient, it would be less desirable or impractical to translate the patient. Therefore, it is possible to combine these elements together by mounting the rapid scanning stage on top of a slow scanning stage and introducing one additional folding mirror that translates along with the slow axis.

Figure 5:
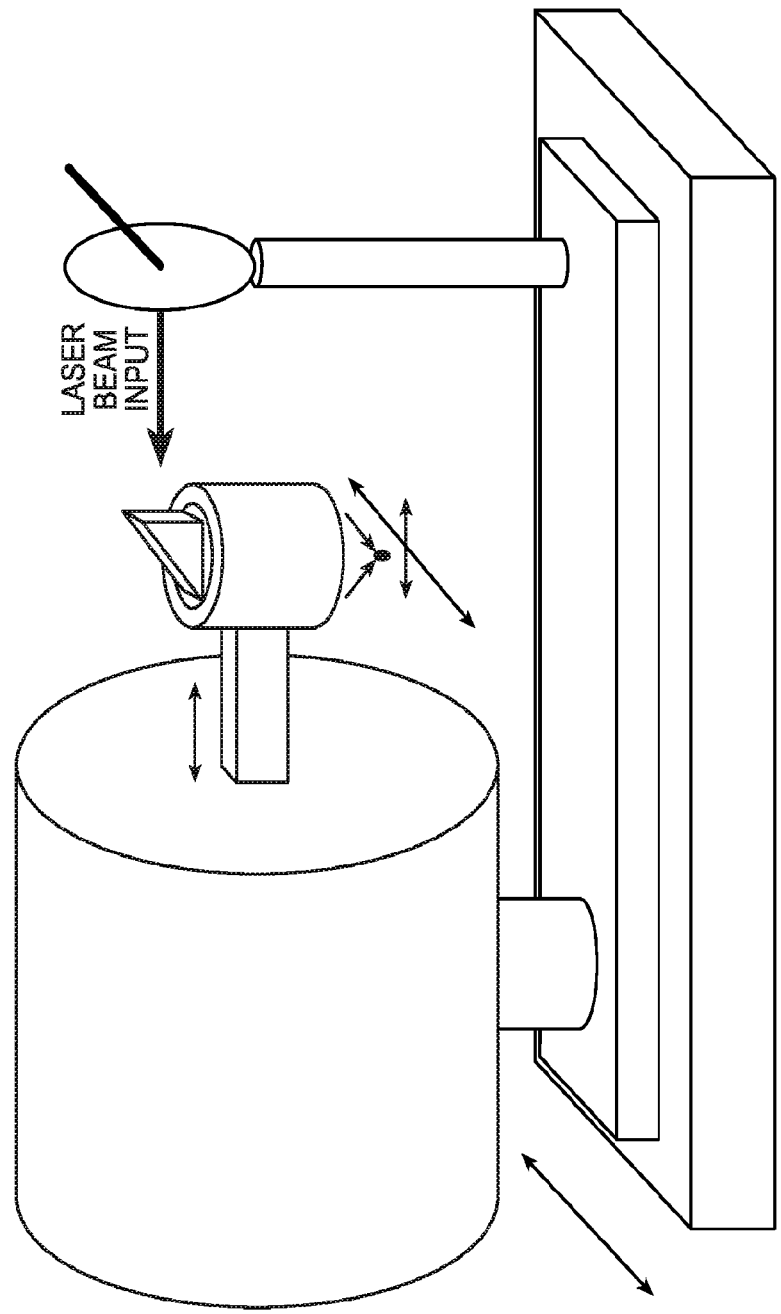
FIG. 5 shows an exemplary embodiment where the fast axis is stacked on top of a slow orthogonal stepping motor where the sample does not need to be translated.

FIG. 5 shows an exemplary embodiment where the fast axis is stacked on top of a slow orthogonal stepping motor where the sample does not need to be translated. This option is believed to be especially suitable for live animal or human surgery. In the configuration of FIG. 5, the beam would be aligned along both orthogonal directions. The previous elements shown in FIG. 3 and FIG. 4 can be incorporated as well, such as double arbitrary waveform generation control or resonant motions with a dual voice coil as well as electro-optic or even acousto-optic modulation control of the intensity.

Figure 6:
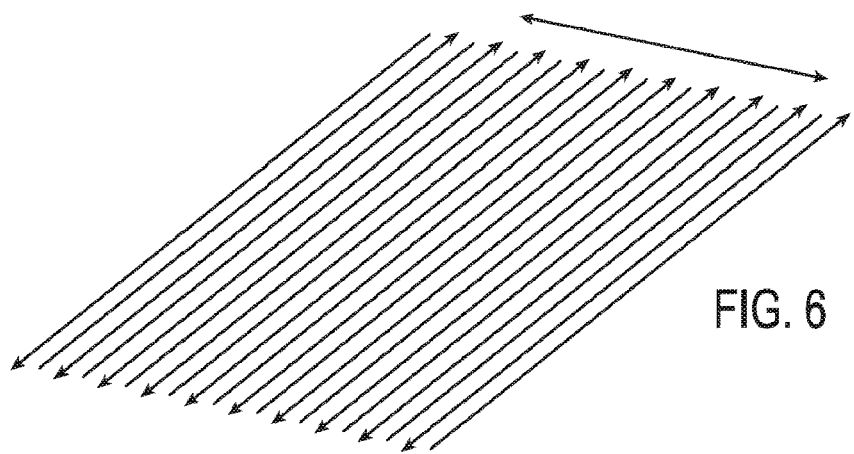
FIG. 6 shows drawing illustrating an exemplary scanning action of orthogonal fast scanning with slow stepping between lines.

FIG. 6 shows a drawing illustrating an exemplary scanning action of orthogonal fast scanning with slow stepping between lines. If the slow stepper is moved at the end of each fast scan, the result is a series of lines. These scan lines fill out a plane (writing a two dimensional refractive index modification) if the sample is not translated vertically during the scanning. The density of lines can be determined by the slow stepper motion and can be varied depending on the desired refractive structure to be written.

Figure 7:
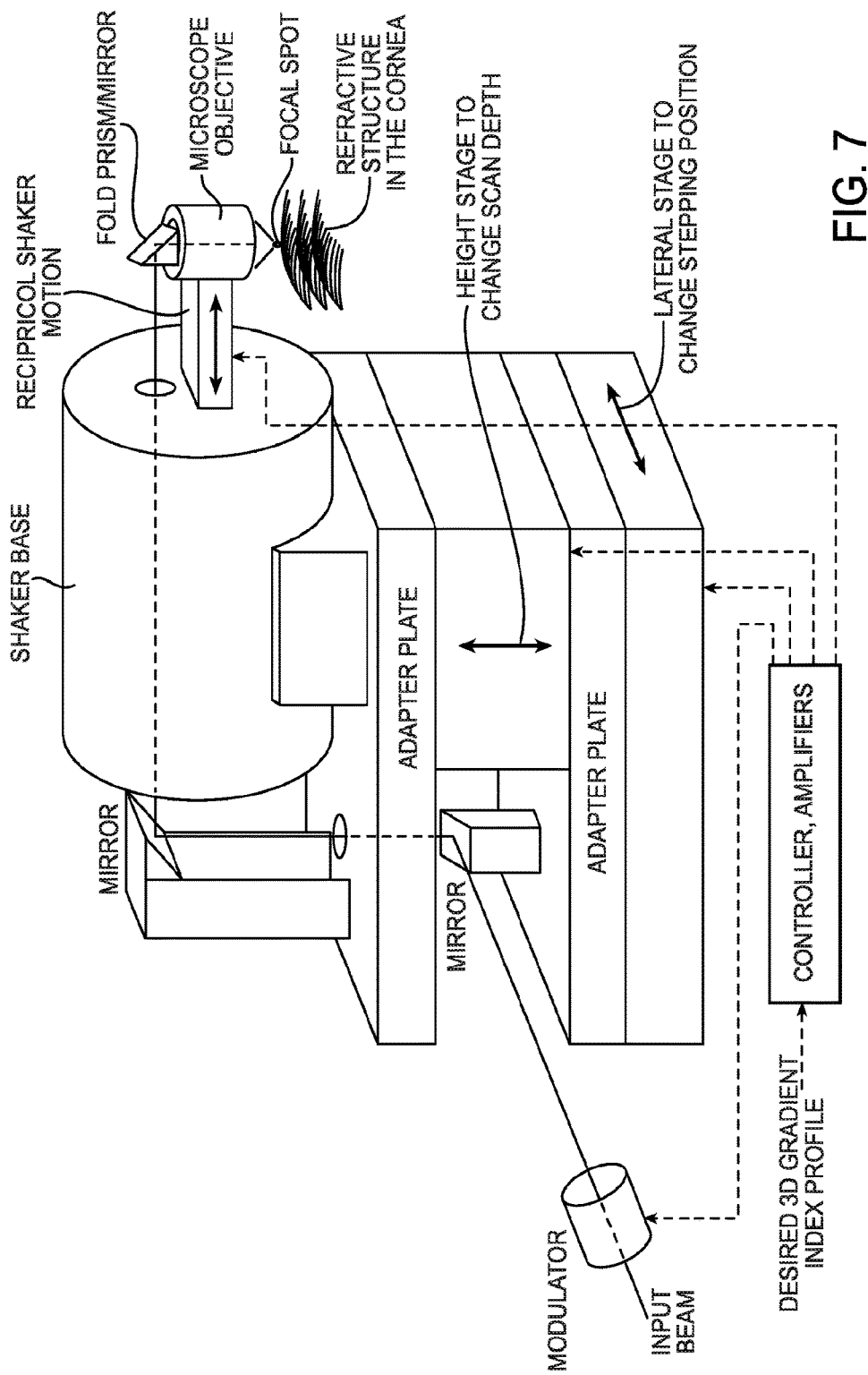
FIG. 7 shows an illustration of an exemplary embodiment where two stacked stages and the shaker stage provide motion in all three axis, yet the sample can remain stationary.

FIG. 7 shows an illustration of an exemplary embodiment where two stacked stages and the shaker stage provide motion in all three axis, yet the sample can remain stationary. Additionally the input beam can be potentially passed through the shaker base to reduce the size of the system. The intensity modulation can occur anywhere prior to the microscope objective, but can also be located before the stages. At the end of the scan the sample can be translated up or down, or the whole scanning apparatus can be mounted on a z-axis scanner as well to write a three dimensional refractive index modification.

Figure 8:
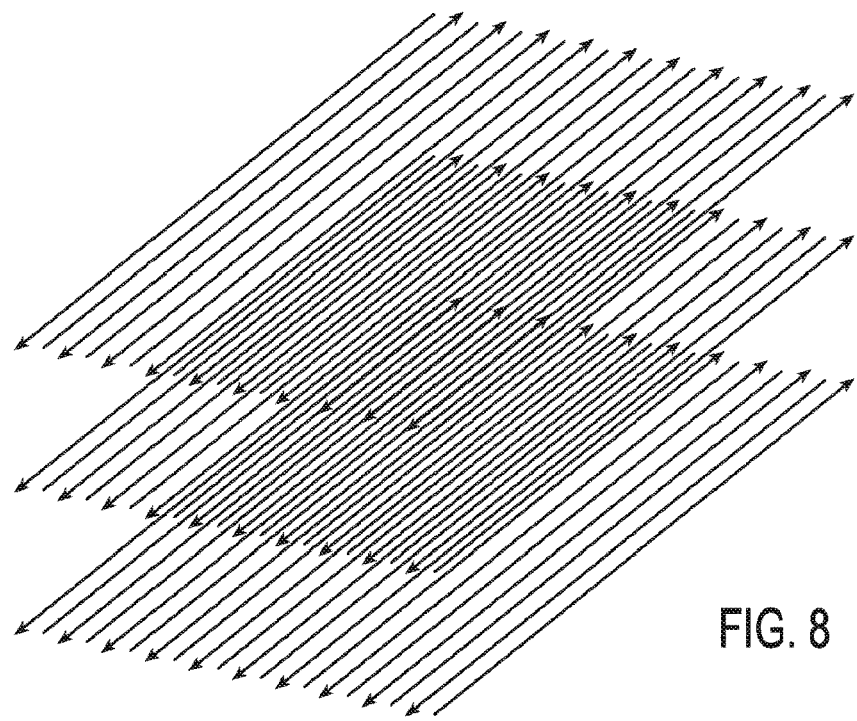
FIG. 8 shows a drawing illustrating how three planes can be written with vertical offsets.

FIG. 8 shows a drawing illustrating how three planes can be written with vertical offsets. Using three (or more) stages will enable positioning on all three axes and the added z-axis (Height Stage) means several layers can be written into the sample, creating the line array patterns as shown in FIG. 8. When stacking the axes, the order does not necessarily matter, so long as the input beam and stage translation are parallel with no lateral shifting during the course of motion. If the refractive index change is made to be different along the slow stepping axis, either by intensity or scanning speed control, it is possible to make a lateral gradient index lens. The density of lines can be determined by the motion parameters in the stepping stage and height stage, which can be varied depending on the desired refractive structure.

Figure 9:
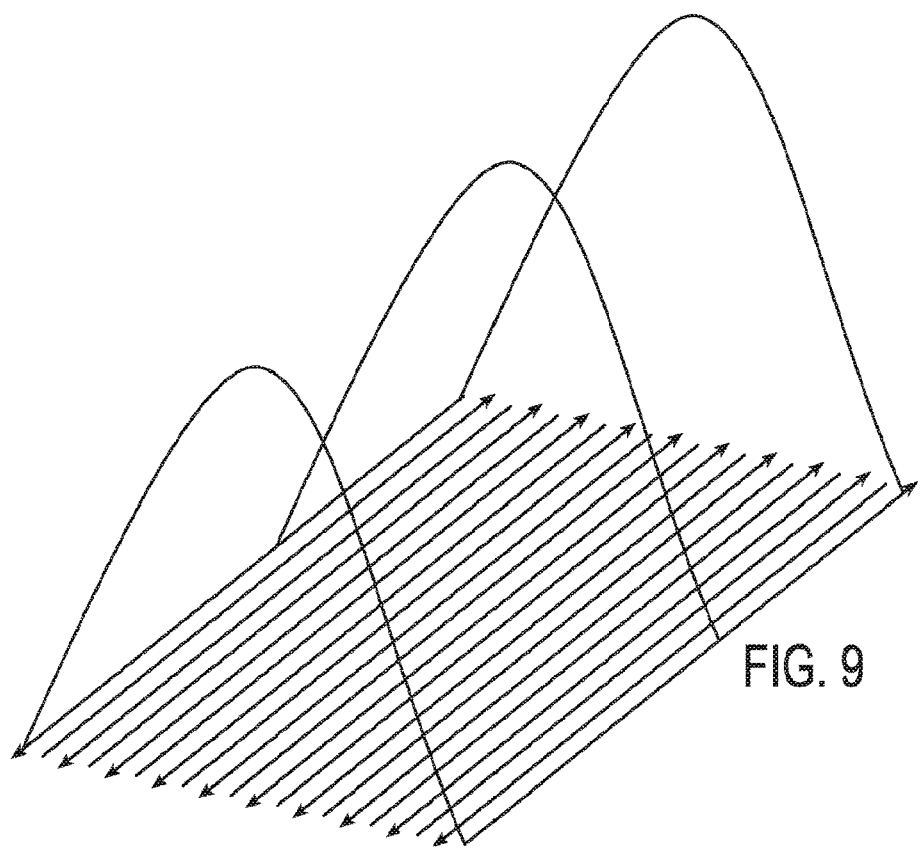
FIG. 9 shows a drawing illustrating a profile of a one dimensional gradient index microlens.

FIG. 9 shows a drawing illustrating a profile of a one dimensional gradient index microlens with a parabolic phase profile using intensity or speed control as a function of slow stepping axis position (a stepping motion). An example of a lateral gradient index lens written using an apparatus such as the exemplary high numerical aperture opto-mechanical scanner for writing refractive index modifications of FIG. 7 is shown in FIG. 9 with a nominally parabolic phase profile. Additional layers can be stacked vertically with small spacings (typically, 5 to 10 micrometers), wherein each layer could be the same, or could be different. Furthermore, if the index of refraction is changed along the fast axis by either fast intensity control and/or with the use of a fast arbitrary waveform to control the fast scan speed along the length, then a fully customized two-dimensional gradient index lens can be written. When writing a parabolic phase profile, such as, for example, by use of an intensity or speed control, the accumulated phase of the written structure can be written in modulo-$2\pi$.

Figure 10:
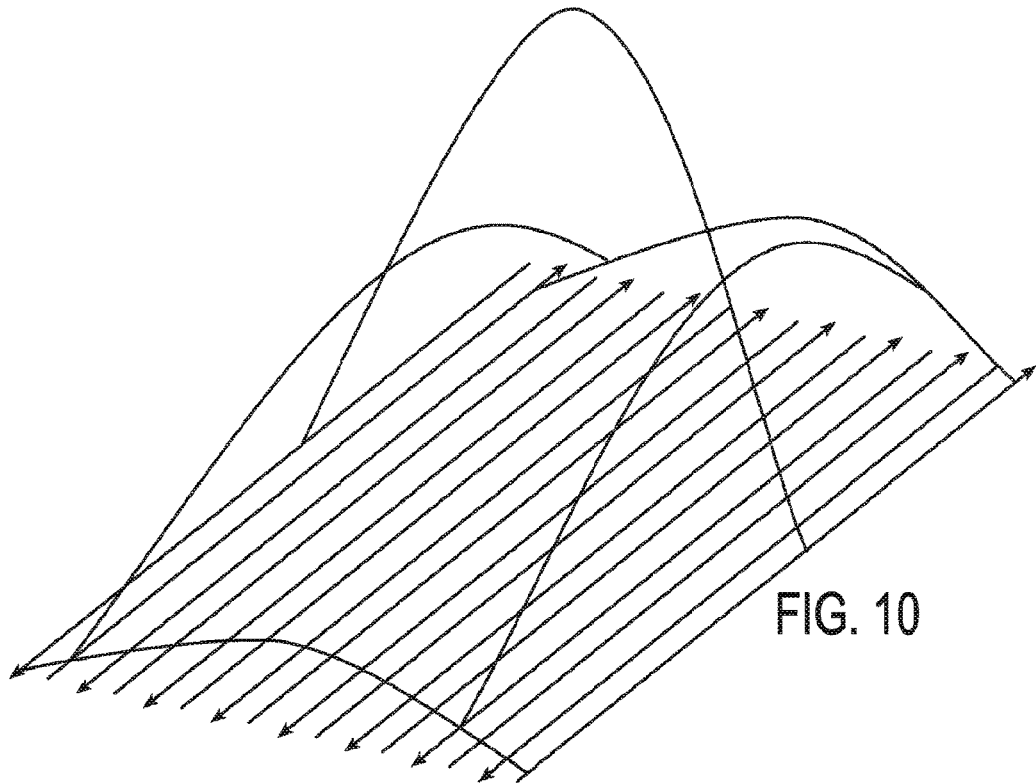
FIG. 10 shows a drawing illustrating the use of fast intensity control and/or fast arbitrary waveform generation.

FIG. 10 shows a drawing illustrating the use of fast intensity control and/or fast arbitrary waveform generation which results in changing index profiles along the length of the lines, and also changes are incorporated along the slow scanning axis. FIG. 10 shows an example of where the index of refraction is changed along the fast axis and along the slow stepping axis as well. The result is a fully 2D gradient index micro lens. In addition, the vertically displaced layers can be made to be different, resulting in effectively a 3D gradient microlens.

Figure 11:
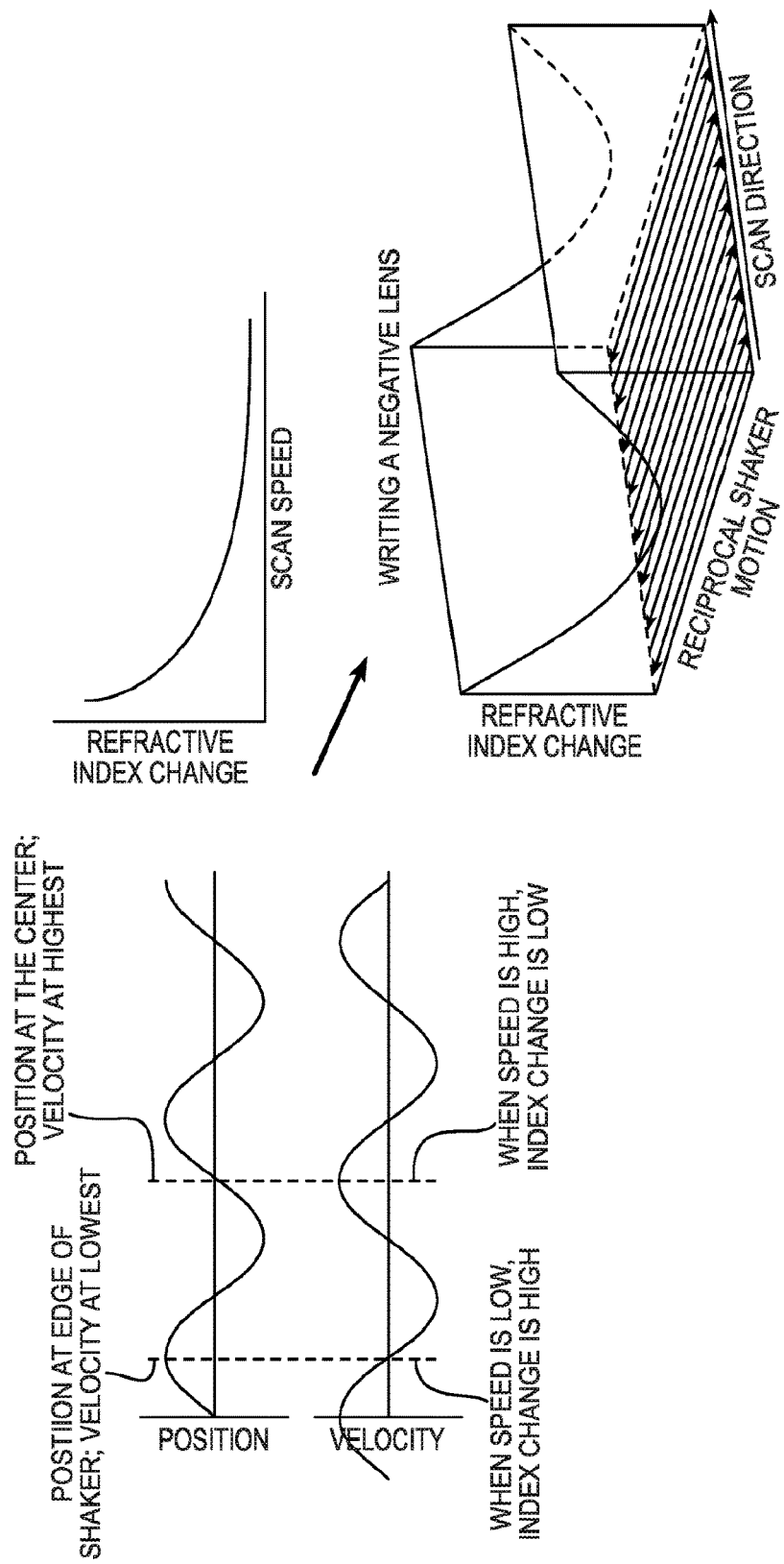
FIG. 11 shows graphs and a drawing illustrating an exemplary method to write a negative refractive index lens.

FIG. 11 shows graphs and a drawing illustrating how a negative refractive index lens can be written using a sine wave to drive the shaker stage. Slower speeds cause higher refractive index changes, which occurs at the turnaround part on the edge. Because the refractive index change is greater when the scan speed is lower, the simplest lens to write is a negative lens. If a simple sine wave drives the shaker stage, then the velocity will be a cosine wave. Thus, the lowest velocity is the turnaround point when the shaker stage is at its motion boundaries, as shown in FIG. 11. Driving the shaker stage with a sine wave and stepping over synchronously (to next line) will yield a negative cylindrical lens.

Figure 12:
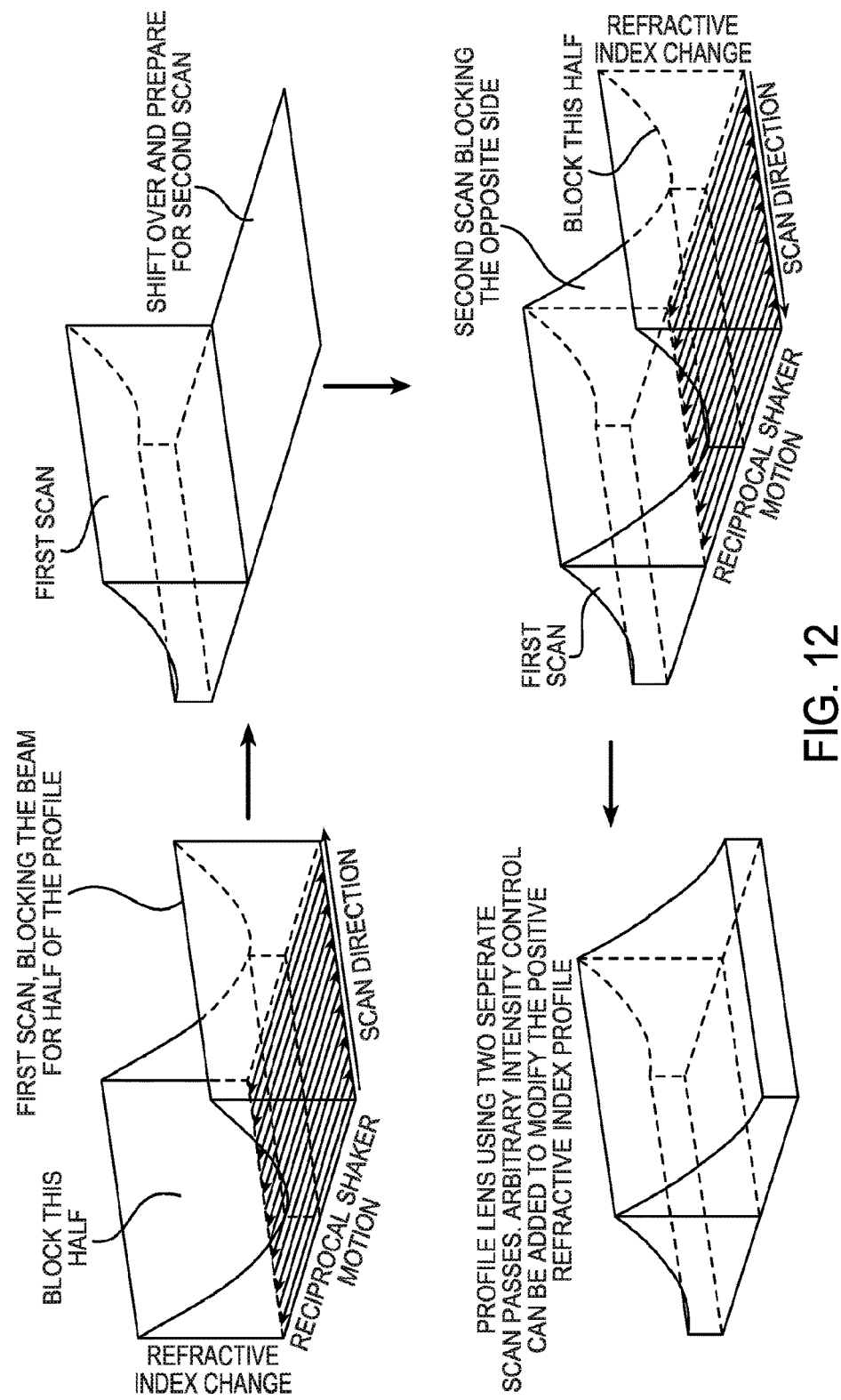
FIG. 12 shows drawings illustrating one exemplary method of writing of a positive lens using a two-scan process.

FIG. 12 shows drawings illustrating one exemplary method of writing of a positive refractive index lens using a two-scan process. The first scan creates half of the profile block. Then the shaker is shifted over and an opposite writing procedure is performed. This method of FIG. 12 results in a positive cylindrical lens. Thus, it can be seen that to write a positive lens without requiring significant input laser power and high speed intensity control, one method is to perform two separate scans as shown in FIG. 12. Instead of writing a negative lens, the starting position in the shaker direction can be offset and the beam can be blocked synchronously to only allow a half cylinder lens to be written. Then the stage system can shift over in position and write a second half cylinder for the opposite side. This will result in a positive cylinder lens.

Figure 13A:
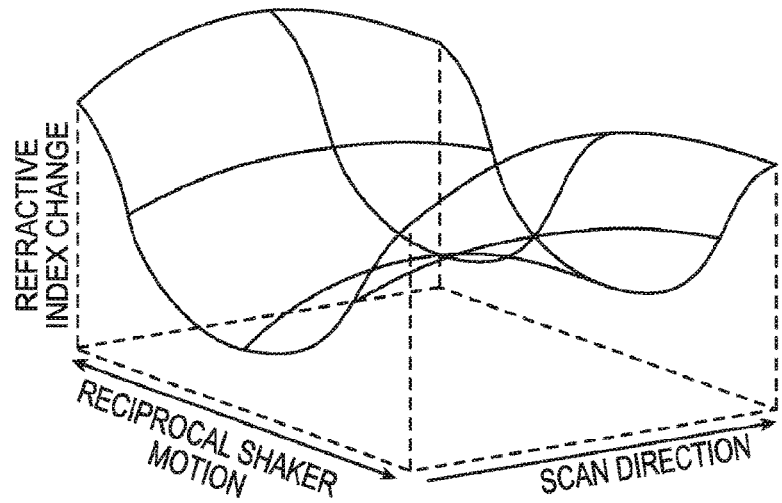
FIG. 13A shows drawings of another exemplary method using high speed intensity control to write negative lenses.
Figure 13B:
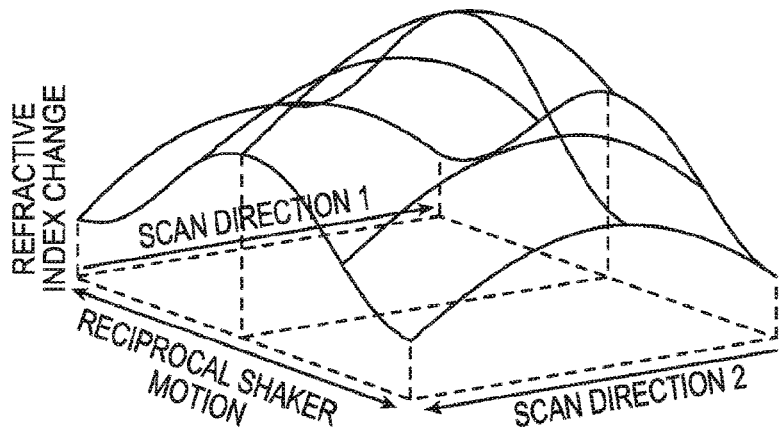
FIG. 13B shows drawings of another exemplary method using high speed intensity control to write positive lenses.

FIG. 13A and FIG. 13B show drawings of another exemplary method using high speed intensity control synchronous with the shaker motion and low speed intensity control synchronous with the scan motion, by which arbitrary negative lenses and/or arbitrary positive lenses can be constructed. A series of arbitrary lenses can then be generated to increase the refractive power of the structure. Thus, both positive lenses (FIG. 13B) and negative lenses (FIG. 13A) (as opposed to cylindrical lenses) can be written using a combination of overlapping lenses and synchronous intensity control with respect to both the shaker and scan axes. The overall refractive power can be tailored to the desired shape using these parameters, as well as global positioning and the laser modulator.

Figure 14:
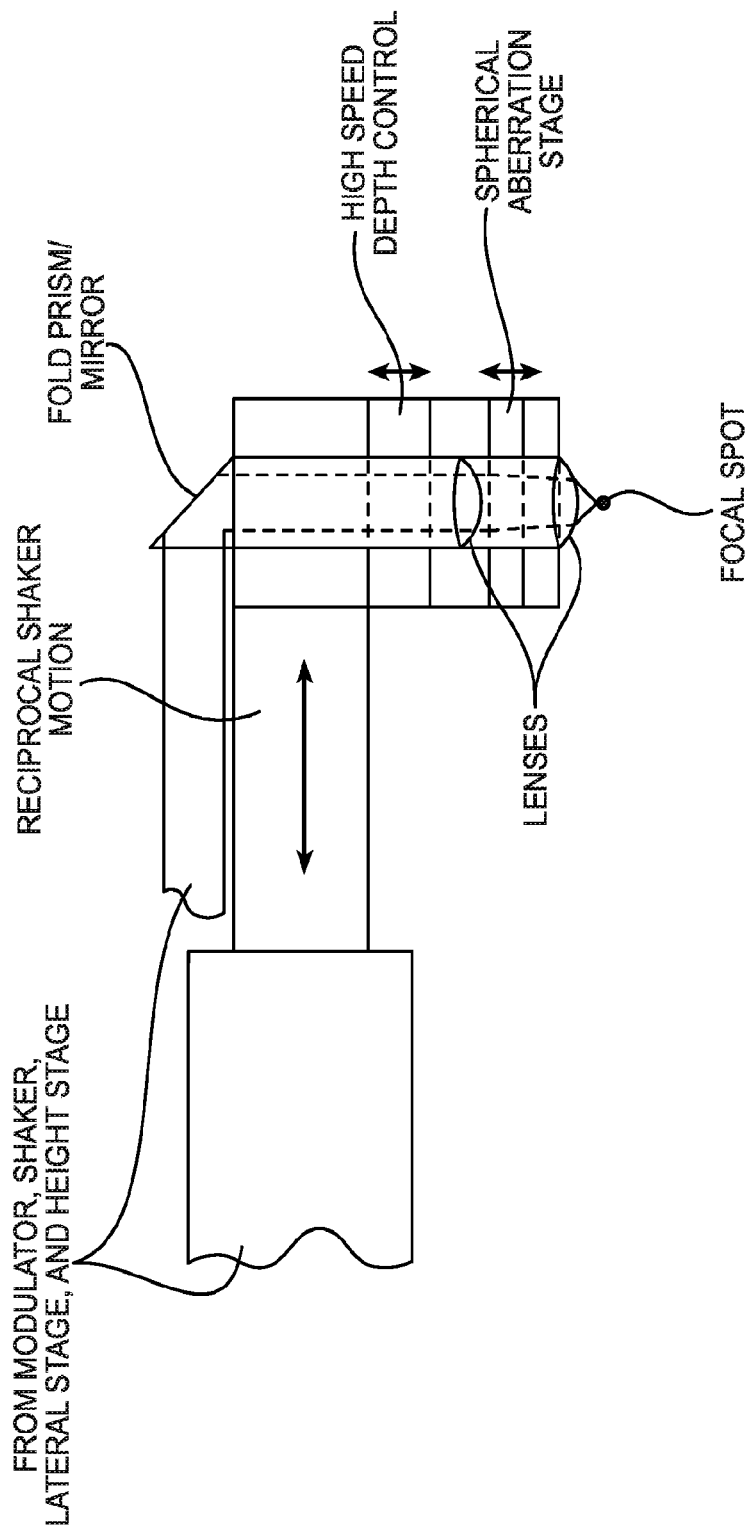
FIG. 14 shows a schematic diagram of a microscope with a high speed depth control stage and a spherical aberration correction stage.

FIG. 14 shows a schematic diagram of a microscope with a high speed depth control stage and a spherical aberration correction stage. The high speed depth control can correct for angular motions of the reciprocal shaker stage. The spherical aberration stage can be used to correct for spherical aberrations to ensure a highly efficient two-photon absorption process to change refractive index in the sample. The microscope objective can contain several stages to help facilitate writing complex structures at high speeds. For example, as shown in FIG. 14, the microscope objective can contain a stage for controlling the depth and a second stage for changing the spherical aberration. These stages are likely in addition to the system discussed in FIG. 3, FIG. 4, and FIG. 7. Also, the input beam to the objective can be modulated using an adaptive optic element to correct for higher order aberrations to improve focal spot quality based on the depth of the focal spot in the material.

Figure 15:
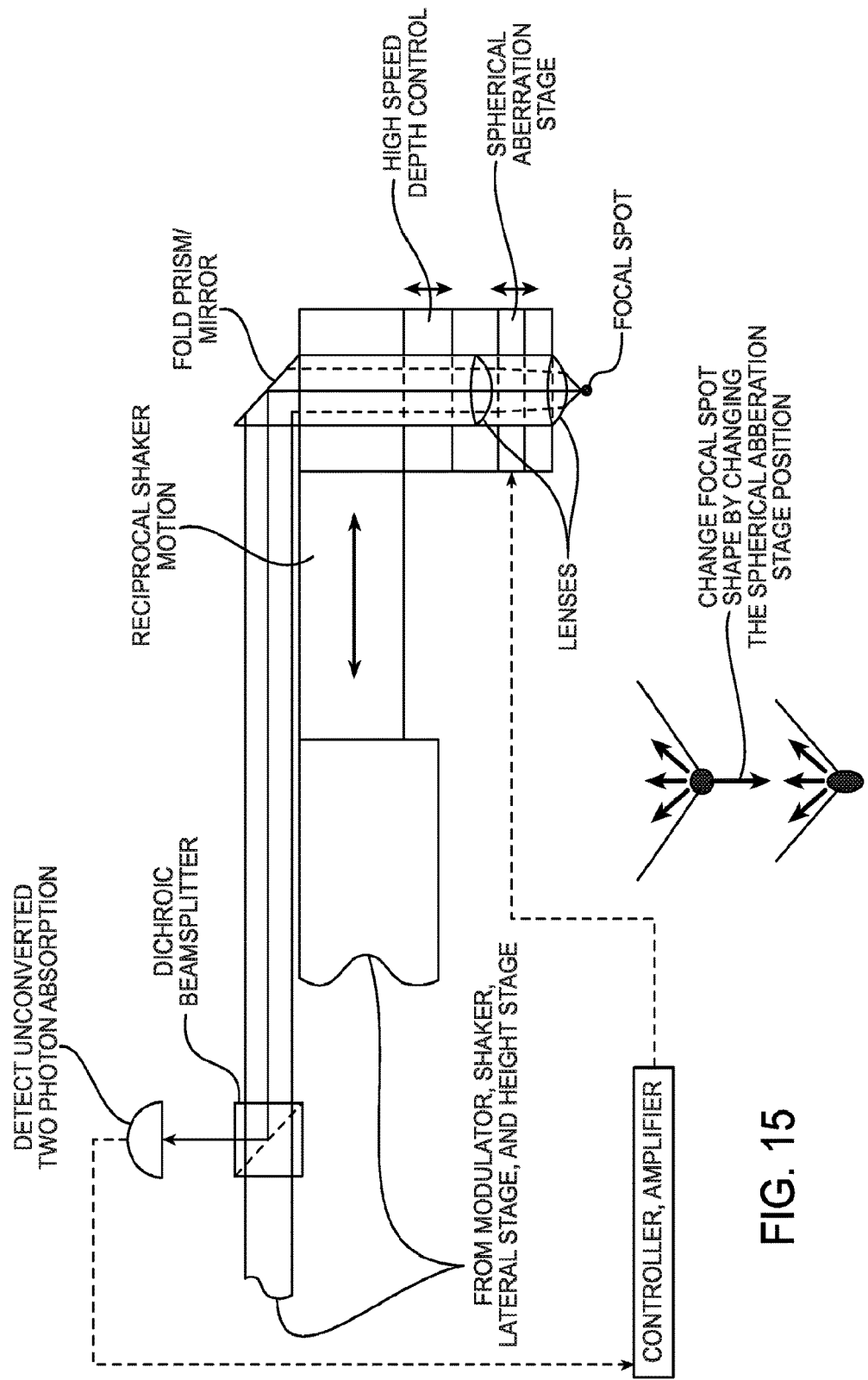
FIG. 15 shows a schematic diagram of a microscope objective changing the focal spot to correct for spherical aberration errors.

FIG. 15 shows a schematic diagram of a microscope objective changing the focal spot to correct for spherical aberration errors. Backscattered light from the unconverted two photon absorption process can be used to determine focal spot quality. This can be fed back into the spherical aberration stage to change the focal spot to improve the efficiency of the conversion process. The unconverted two photon absorption can be used as a metric for determining the amount of spherical aberration. Some of the backscattered light can be collected, split from the input beam, and detected, as shown in FIG. 15. This information can then be fed into a controller to change the spherical aberration stage to adjust the focal spot to ensure a tight, spherical spot with high efficiency, rather than an elongated spot. As several layers will likely be necessary to build refractive index structures with significant refracting power, ensuring a small, spherical focal spot will increase the conversion process and efficiency.

Figure 16:
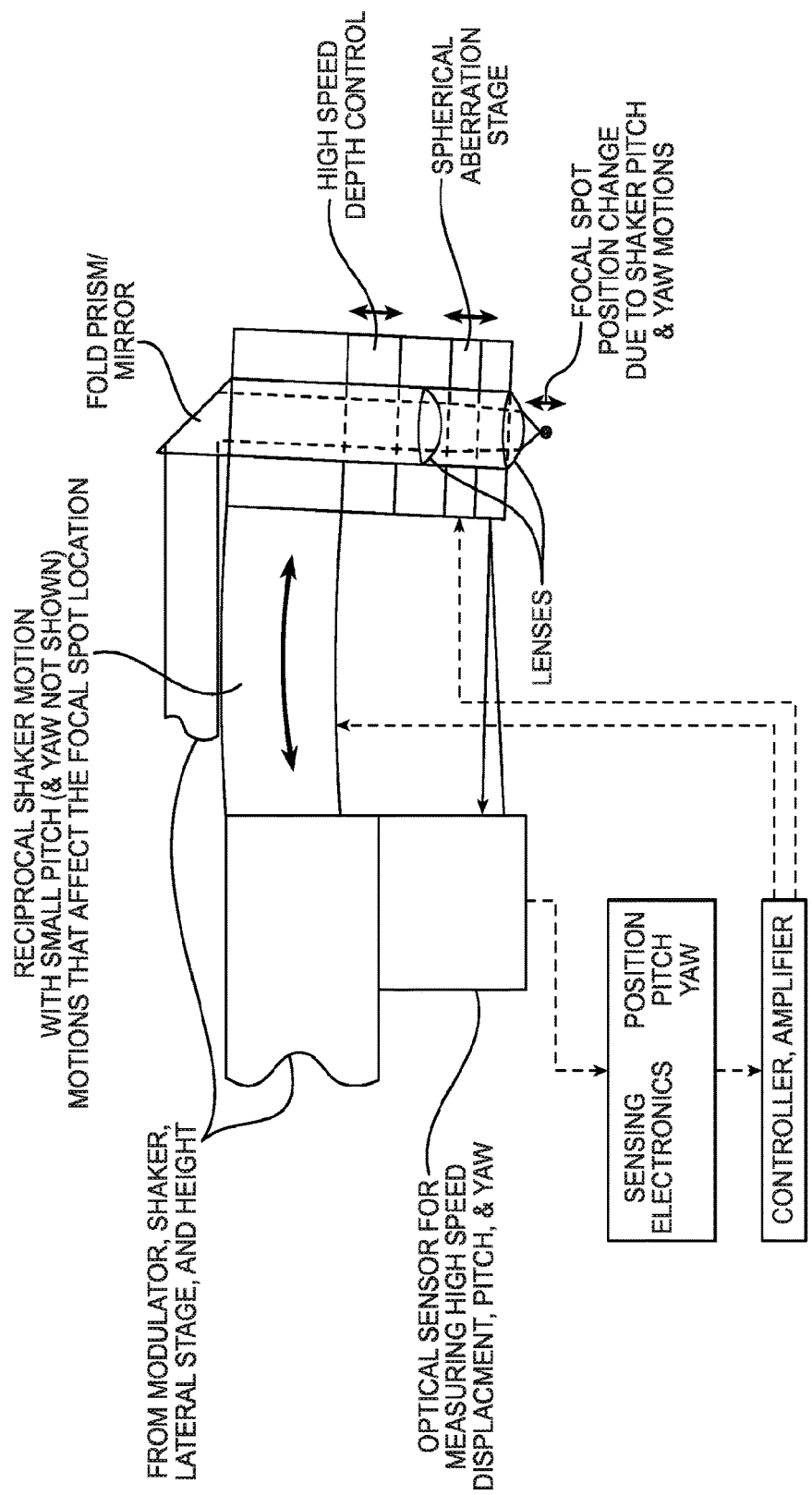
FIG. 16 shows a schematic diagram of an exemplary embodiment for correcting small pitch and yaw errors.

FIG. 16 shows a schematic diagram of an exemplary embodiment for correcting small pitch and yaw errors by changing the microscope objective height as the reciprocal shaker stage traverses across the same. The small mass of the microscope objective means the lenses can be positioned synchronously with the motion of the shaker stage. The depth control stage can be used to ensure the focal spot is at that correct depth. Slight imbalances in the mass distribution of the microscope objective can create small pitch and yaw motions, as shown in FIG. 16. These small pitch and yaw motions lead to an error in depth for the focal spot. These angular motions can be calibrated assuming the amount of pitch and yaw error can be measured at the same time as the position. This can be accomplished using, e.g., a three axis interferometer with a single beam measuring the position [6]. Additionally, this can be measured in-situ and corrected in real time provided the High Speed Depth Control Stage has a sufficient bandwidth to keep up with the Shaker Stage. This is an enhancement of the position feedback was described hereinabove with respect to FIG. 4. Thus, a high numerical aperture opto-mechanical scanner can have one or more of any suitable sensors, such as, for example, an optical sensor that provides a measurement of displacement, straightness, pitch, yaw and/or roll of the scanning lens assembly to correct a position of the scanning lens assembly during scanning.

Figure 17:
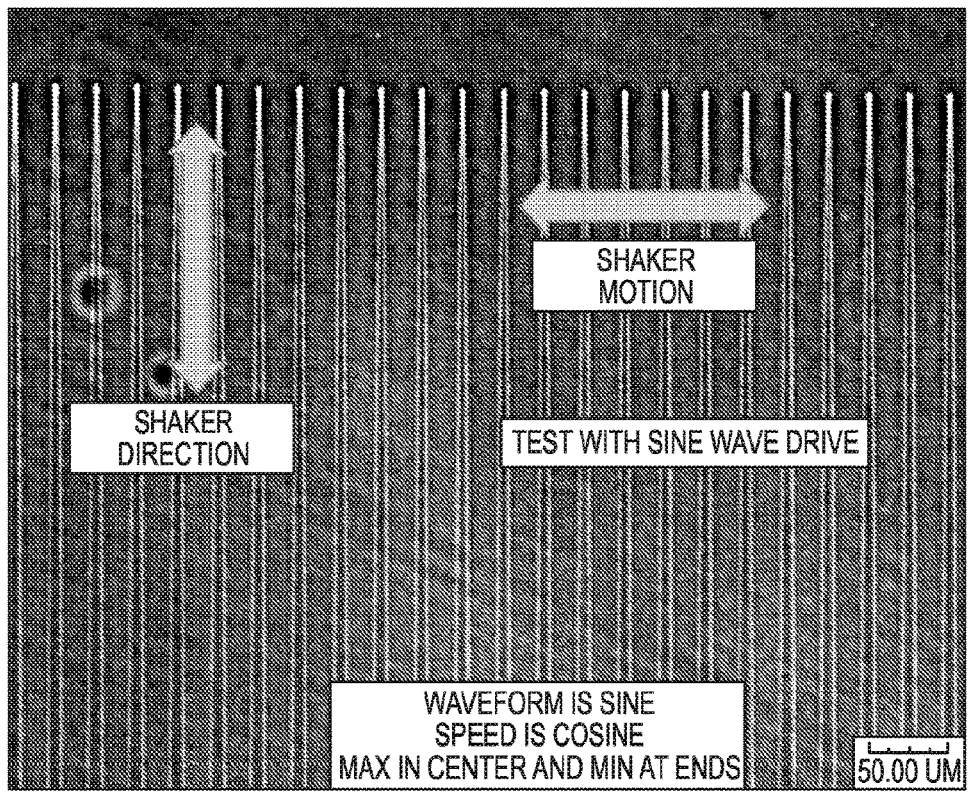
FIG. 17 is an illustration showing an exemplary sample written while driving the fast axis with a sine wave.

FIG. 17 is an illustration showing an exemplary Akreos:X monomer sample written while driving the fast axis with a sine wave at around a 10 Hz frequency. In a preliminary demonstration of this system, we used frequencies of about 5-22 Hz, laser power of a few hundred milliwatts, 800 nm wavelength, Akreos:X monomer sample in solution and a LUCPlan0.70 microscope objective. FIG. 17 shows the result of a differential interference contrast photo of the Akreos:X sample after writing a pattern of index change using a pure sine wave while slowly translating the stepper motor asynchronously along the slow axis. The result is a nice sine wave, as expected.

Figure 18:
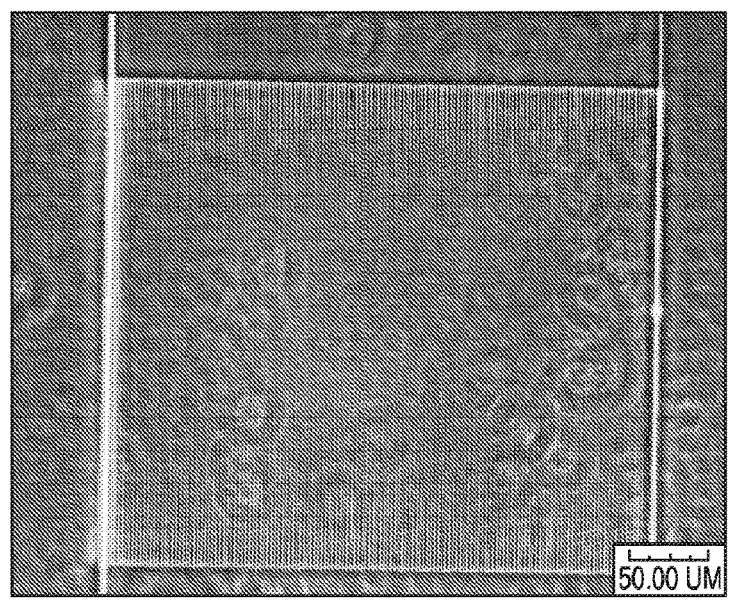
FIG. 18 is an illustration showing exemplary writing with a slower lateral stepping speed.

FIG. 18 is an illustration showing exemplary writing with a slower lateral stepping speed, which can be used to write a denser array of lines. By slowing down the slow axis stepping, a much denser array of lines can be achieved, as shown in FIG. 18. Because the waveform is a sine wave, the velocity is a cosine wave, and therefore the index of refraction changes are larger near the ends where the velocity is low, as expected.

Figure 19:
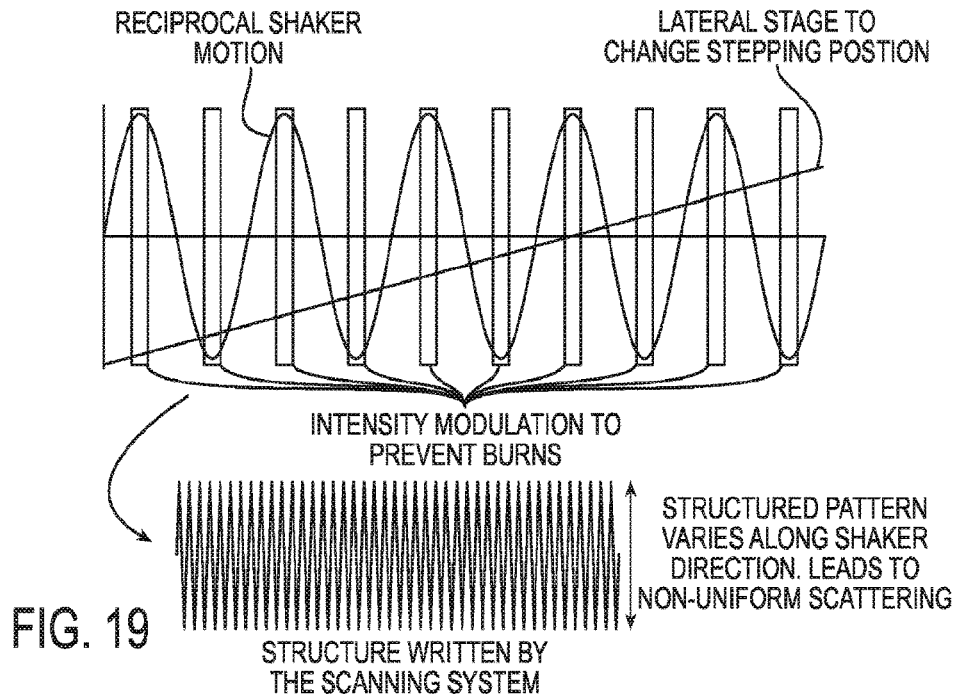
FIG. 19 shows graphs illustrating an exemplary shaker stage driven with a sine wave and a lateral scan stage translating in a linear fashion.

FIG. 19 shows graphs illustrating an exemplary shaker stage driven with a sine wave and a lateral scan stage translating in a linear fashion. Intensity modulation can be synchronized with the shaker motion to reduce the high refractive index change at the turn around points. This creates the scan pattern in the bottom of the FIG. 19 with a non-uniform step over based on the shaker position. In a current experimental system, the shaker stage is driven with a nominal sine wave while the scan stage is linearly displaced, as shown in FIG. 19. This results in a structure that varies in spacing as function of the shaker stage position as was also shown in FIG. 17. Because the shaker stage is driven with a sine wave and the scan stage is driven linearly, the turnaround points on the shaker stage overlap while the center of the shaker stage has an even distribution in the scan direction. This overlap causes large changes in refractive index because the shaker velocity goes to zero. This can be corrected by applying intensity modulation via a shutter, acousto-optic modulator, electro-optic modulator, or attenuator synchronized to the shaker motion.

Figure 20:
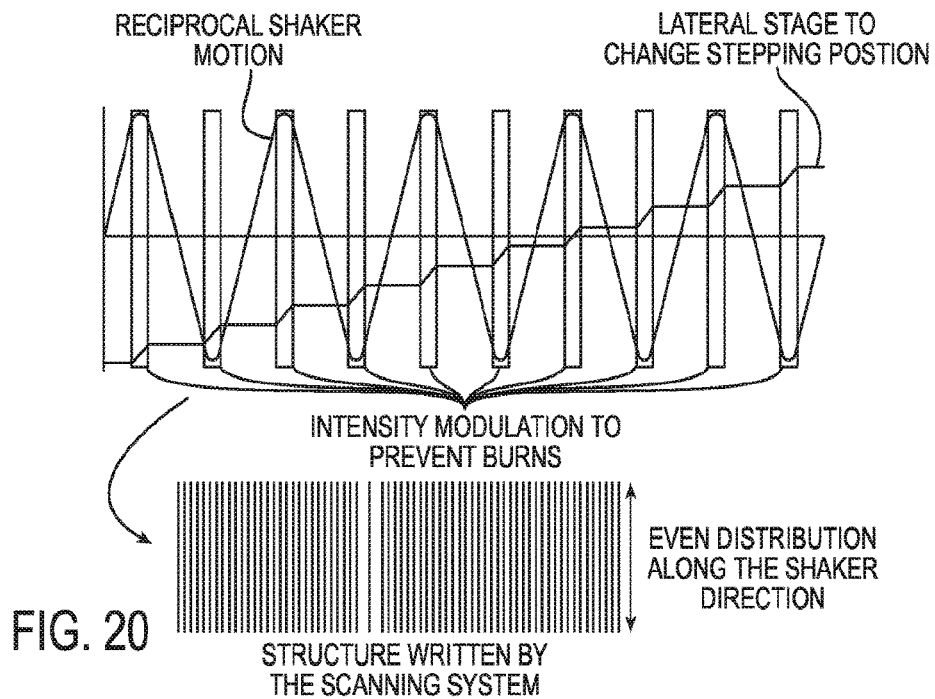
FIG. 20 shows graphs illustrating an exemplary shaker stage driven with a modified sine wave and lateral can stage.

FIG. 20 shows graphs illustrating an exemplary shaker stage driven with a modified sine wave and the lateral stage can be synchronized to step over at the shaker stage turnaround points. This creates the scan patter with a uniform step over based on the shaker position. This alternative method applies a modified sine wave to the shaker direction that has a linear position change followed by rapid turnaround points. Intensity modulation is still synchronized at the turnaround points to prevent high refractive index changes or damage as needed. The lateral scan stage is also synchronized to the shaker stage by remaining stationary while the shaker is moving with constant velocity and rapidly steps over when the turnaround point is reached as depicted in FIG. 20. The structured pattern that results from this scanning method is uniform lines with a constant step over distance along the shaker direction. Subsequent layers can be written in the same focal plane but interleaved with the vertical scanned structure to increase the structure density and reduce scattering. Also, this pattern can be written in the orthogonal direction by rotating the complete scanning system 90 degrees.

Figure 21:
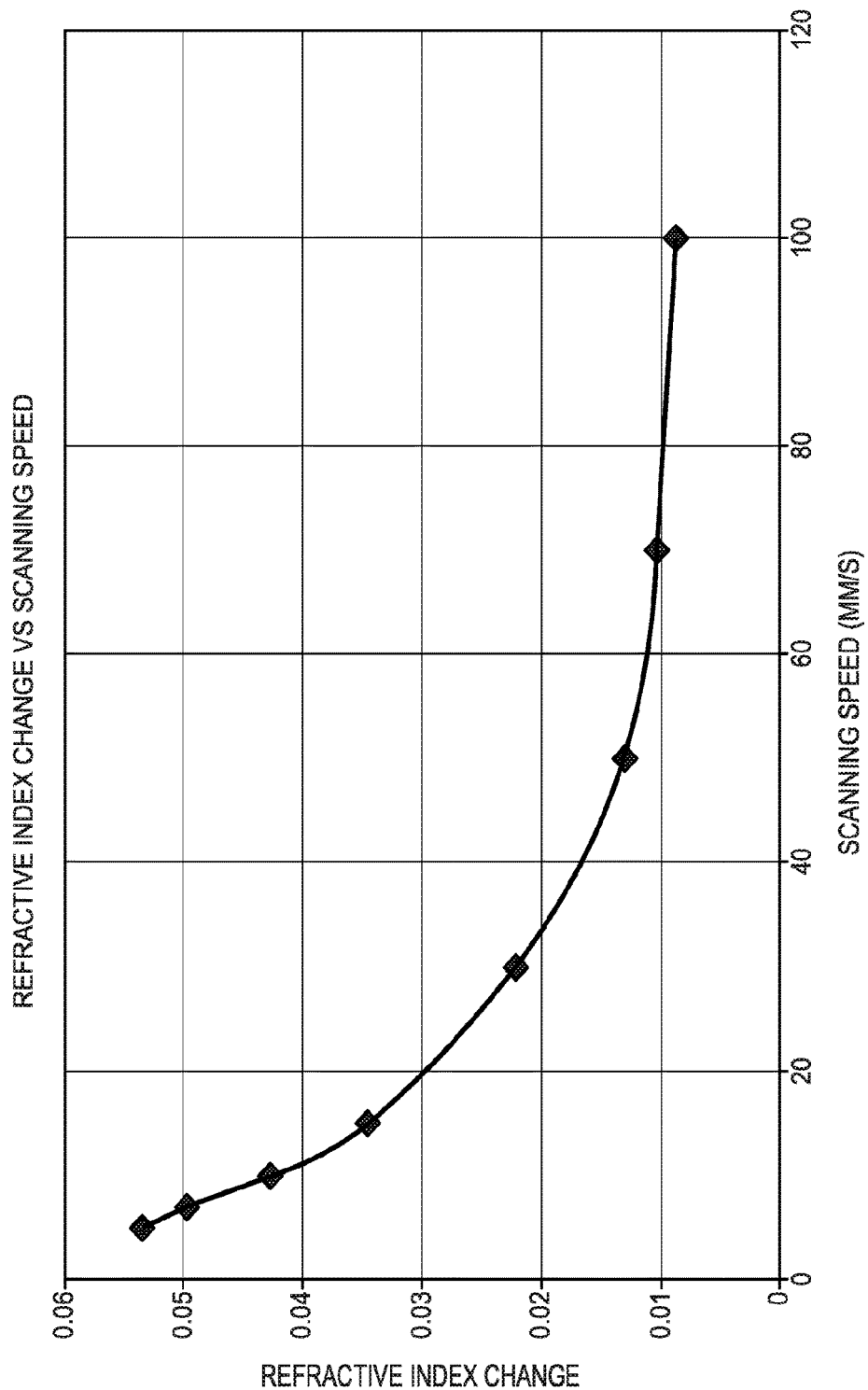
FIG. 21 shows a graph of measured index of refraction change versus scan speed.

FIG. 21 shows a graph of measured index of refraction change versus scan speed in exemplary Akreos:X at about 350 mw power, about 800 nm wavelength and NA about 0.7. In order to write desired structures for custom vision correction, processes can be provided that take into account the scan speed dependence of the index of refraction change, as shown in FIG. 21.

Further expected improvements should come from an optimization of the characteristics of the focusing lens. The microscope objective that is currently being used is in fact fully corrected for chromatic aberration (which is not needed), astigmatism to full field angle (which is not needed, since we operate only at zero field angle), and coma to full field angle and aperture (which is also not needed.) There is one important correction which we do use, and that is a variable spherical aberration, which is adjusted depending on the depth of the written layer. Therefore, it should be possible to develop a single element aspheric objective that would be much smaller and lighter, as long as it can provide a variable level of spherical aberration correction, it should be much smaller and lighter, and therefore facilitate much more rapid scanning and improved throughput performance. Furthermore, the spherical aberration and defocus could be rapidly changed with a small deformable adaptive optic element that is folded into the incoming beam path. Active feedback using a two-photon fluorescence or other nonlinear signal could be used to control the adaptive optic element.

It is contemplated that gradient index corrective layers might be written in non-planar layers. In such cases, it would be desirable to couple the z-axis position of the lens or the sample to the scanning of x- and y axes. This could be accomplished in several different ways. In fact, focusing lenses for portable compact disc players use some kind of active feedback voice coil technology that could be adapted for this purpose.

It is also contemplated that the optical beam delivery system involving folding mirrors could be replaced by a short length of flexible optical fiber.

Figure 22:
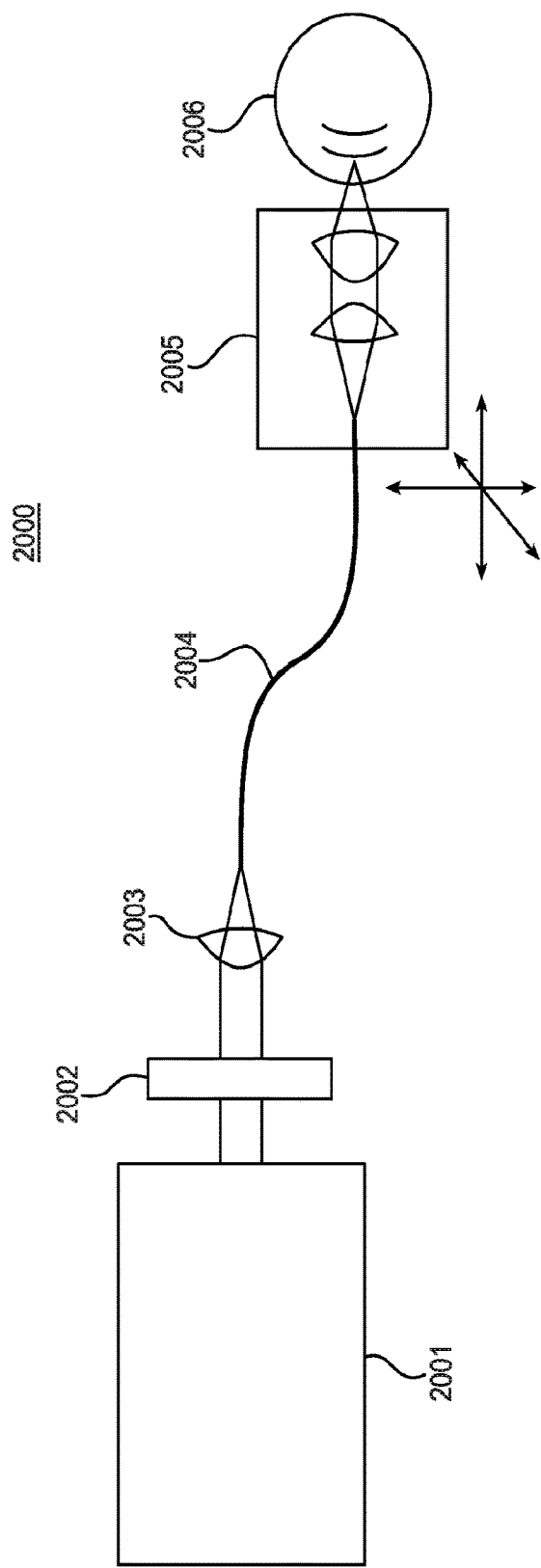
FIG. 22 shows a block diagram of an exemplary fiber-coupled beam delivery system.

FIG. 22 shows a block diagram of an exemplary fiber-coupled beam delivery system for writing 3D structures at high speed. The femtosecond laser beam can be coupled into the optical fiber (as shown in FIG. 22) after passing through a high speed acousto-optic or electro-optic intensity modulator.

Use of a single-mode fiber is advantageous in ensuring good beam quality at the output, although a number of optical fiber types are possible. If ordinary single-mode fiber is used, at the typical intensities used for writing blue-fs IRIS structures in the eye, significant nonlinearity would be accumulated after only 1.3 cm propagation. This would lead to pulse distortion and reduced writing efficiency. Multi-mode optical fibers could be used if the input beam is mode-matched to only the fundamental mode of the multi-mode fiber, and this could be advantageous in the case of multi-mode fibers that are designed to have a large fundamental mode size, as long as the higher order modes are not excited by scattering processes. Advantageously, a new photonic crystal fiber that is designed to support only the fundamental mode with a large mode area may be used. Kashiwagi [7] describes an effectively single-mode fiber with effective area of 650 $\mu m^2$, which is ten times as large as the effective area of a typical single mode optical fiber. This fiber was able to be bent in a 10 cm radius while transmitting the fundamental mode with low loss. Using such a fiber, about a 10-13 cm length would have acceptable nonlinear phase accumulation. This would result in a more compact beam delivery system.

Wang [8] describes a mechanical scanner for photoacoustic spectroscopy that includes a conventional single mode fiber delivery system, however that system does not use femtosecond lasers pulses for nonlinear absorption, so nonlinearity is not a limitation in the single-mode fiber in that system. Furthermore, Wang does not include intensity control and does not create index of refraction modifications as a result of the scanning.

EXAMPLE

Continuing our description of a precision large field scanning system for high numerical aperture lenses and application to femtosecond micromachining of ophthalmic materials, a precision, large stroke (nearly 1 cm) scanning system was designed, built, and calibrated for micromachining of ophthalmic materials including hydrogels and cornea (excised and in vivo). This exemplary system includes a flexure stage with an attached objective on stacked vertical and horizontal translation stages. Following a brief introduction, the design process leading to our most current version including the specifications that were used in the design and the drawbacks of other methods that were previously used is described hereinbelow. Initial measurements of the current version are also given. The current flexure was measured to have a 27 Hz natural frequency with no load.

Introduction: As described hereinabove, traditionally, optical structures with refracting power, such as lenses, are made of a material with homogeneous properties where the refractive index (RI) and curvature of the surfaces determine the amount of refracting power [9]. For example, in ophthalmic applications, different curvatures and higher order shapes can be used to generate desired prescriptions in devices such as eyeglasses, contact lenses, and intraocular lenses, with materials such as glasses and plastics with different index of refraction.

Changing the curvature is not the only way to induce changes in optical power. The optical power of an object can also be adjusted by spatially changing its refractive index. Thus, if the refractive index can be changed in a spatially controlled manner, refractive power can be induced even if there is no curvature to the surface, creating a Gradient Index (GRIN) material [9]. GRIN materials have traditionally been made by diffusing one material into another, which is a generally a bulk process with limited ability to finely tune local refractive index values. To change the refractive index of a material on a highly localized scale, alternative methods such as laser processing are needed.

In the past few decades, femtosecond laser pulses have been used to create microstructures in various materials [10-15]. The femtosecond micromachining process utilizes nonlinear absorption to cause material changes on the micrometer scale. Since this absorption only occurs in the focal region, it has very good three dimensional writing capability. Femtosecond micromachining has thus been used to create a variety of GRIN devices including optical waveguides, light couplers, and 3-dimensional optical storage structures [16-18], but the index changes reported were small—on the order of $10^{-4}$ to $10^{-2}$ in glasses and plastics [10-20].

More recently, Ding and colleagues showed that refractive index changes as large as +0.06 could be created in ophthalmic materials such as hydrogels, using writing speeds initially as slow as 0.4 µm/s [21]. These initial writing speeds were so slow that it would be impractical to use this method for writing millimeter scale devices such as those required for vision correction. Later, the same team discovered that by doping with certain dyes or co-polymerized two-photon absorption enhancers, that enhanced the two-photon absorption of the material, the writing speed could be increased dramatically [22, 23], while moving the focal spot as fast as 100 mm/s [32]. The largest refractive index change reported using this method was 0.08 [23]. With the increase in writing speed, it became feasible to create larger structures. The localized change in index of refraction is dependent on the energy deposited in the focal volume, which is determined through a nonlinear interaction by the intensity in the focal spot and speed of translation of the focal spot. By raster scanning a sample under a high-numerical aperture (NA) microscope objective (necessary to achieve a high localized energy deposition for the nonlinear process), it was possible to create a lateral gradient index lens in the hydrogel [24]. This has applications in areas such as customization of contact lenses and intraocular lenses. Furthermore, this process has also been shown to work in living corneal tissue where it has been termed Intra-Tissue Refractive Index Shaping (IRIS) [25-27].

One of the limiting factors in applying this micromachining process to actual contact lenses and cornea is the lack of a scanning apparatus that meets the stringent demands of the process and application, e.g. large NA lenses (NA≥0.7) while scanning an area up to 8 mm in diameter at high speeds (up to 500 mm/s). In the past, several different scanning methods have been used to write RI structures in hydrogels and cornea. The first method involved a galvanometer-based scanning system which used two oscillating mirrors located at the entrance pupil of a high NA objective (NA=0.7). This scanning method gave excellent control over the focal spot, along with sufficient speed and acceleration, but it could only cover an area approximately 300 µm in diameter [22]. The scanning region could be increased, but to cover the required 6-8 mm diameter area needed for most ophthalmic applications, the cost would be prohibitive. This is because it would require high-performance custom optics to accommodate the field angles necessary at the required NA.

Figure 23:
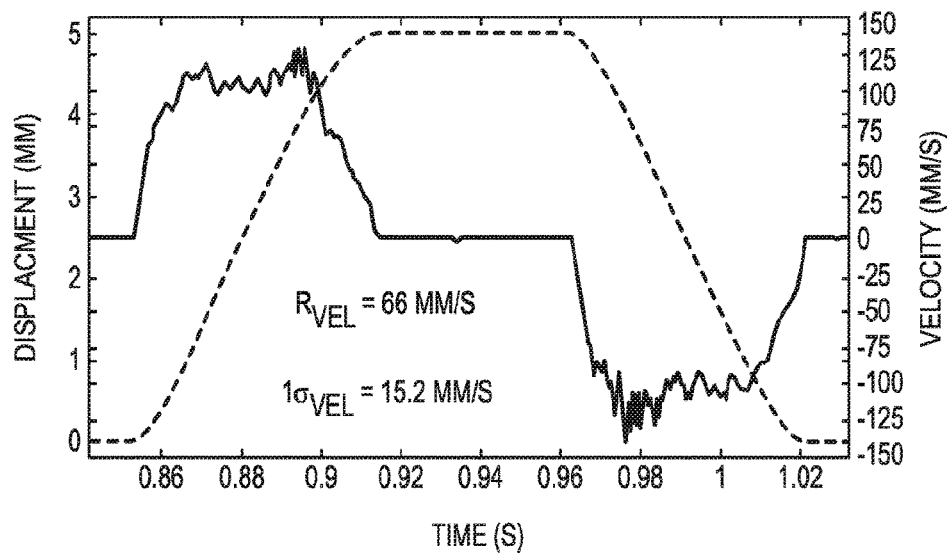
FIG. 23 shows a graph of displacement and velocity versus time for piezo stepper stage.

An alternative scanning system that has been previously used [22] involved a stacked piezoelectric stepper stage assembly using two orthogonal stages, which had a large travel area, and either moved the sample or the scanning objective, thereby decoupling the field size from the NA of the objective lens. Such a scanning system, with a fixed microscope objective and moving sample, is suitable for proof-of-concept studies, but less so for clinical applications. Moreover, we found that the translation speed of the stages used was highly variable; the standard deviation was 15 mm/s at a nominal speed of 100 mm/s, and there was a high degree of variability in interpreting the point where constant velocity begins. An exemplary scan speed profile of a PILine M-663.465 piezo stepper stage is shown in FIG. 23. FIG. 23 shows a graph of displacement and velocity versus time for piezo stepper stage. In FIG. 23, the scan speed profile of a PILine® M-663.465 piezo stepper stage has a displacement of 5 mm and a nominal speed of 100 mm/s. Once "constant velocity" is reached, the 1σ standard deviation was 15.2 mm/s with a range of 66 mm/s.

Figure 24:
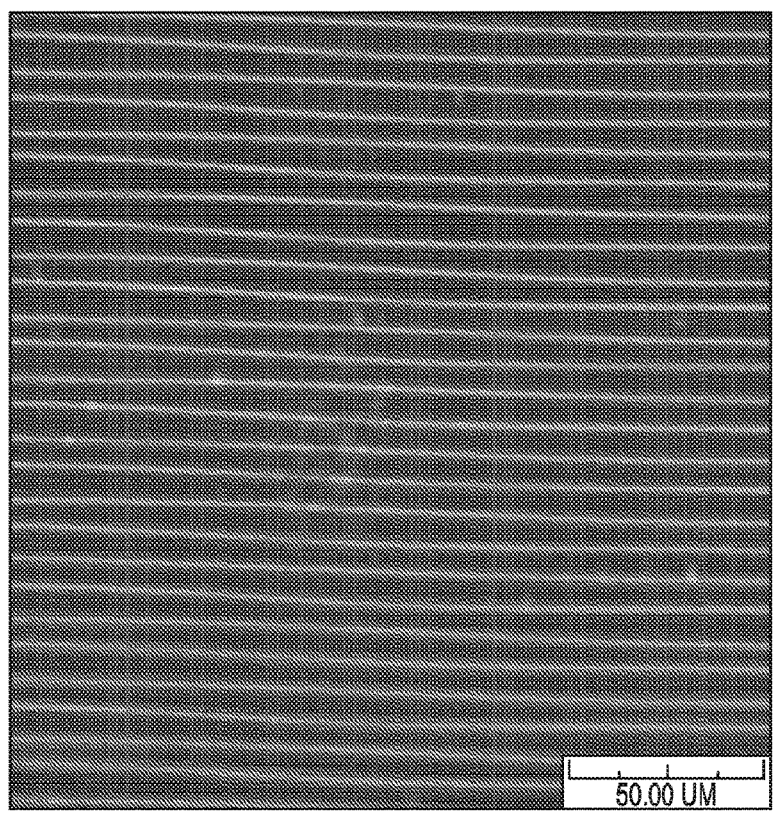
FIG. 24 shows a DIC microscope image illustrating lateral positional inaccuracies in the piezo stage in hydrogel.

In addition to the variability in the linear scan speed, at higher velocities we observed lateral positional inaccuracies much larger than the width of the individual lines of index change. FIG. 24 shows a DIC microscope image illustrating lateral positional inaccuracies in the piezo stage in hydrogel. The picture of FIG. 24 was taken with a differential interference contrast (DIC) microscope of the RI lines written in Bausch+Lomb Akreos:X hydrogel polymer, using stacked piezo stepper stages. A DIC microscope allows direct visualization of the localized RI changes induced in normally transparent material.

The variations in speed result in variations in RI change, since the resulting localized RI change decreases monotonically with scan speed [22]. These variations, combined with lateral positional inaccuracies that can be seen clearly in FIG. 24, also result in a net optical scattering produced by the resulting GRIN structures that is undesirable for vision correction devices. In addition to a loss of visual contrast of any image viewed through such a structure, optical scattering also causes difficulties in measurement of the optical properties of any structures inscribed.

Because commercially available X-Y-Z scanning systems are either too slow, too inaccurate, or write over too small an area, we turned to flexure-type scanning systems. We first demonstrated a preliminary prototype scanning system using a commercial vibration exciter and then designed a custom flexure stage to increase the writing velocity and field size [28]. In this paper, we present optical device results from the first prototype scanning system, which aided in determining the desired specifications for a custom large-field scanner. We also present results from the initial qualification of a large field scanner that we believe is suitable for writing GRIN structures over a sufficiently large field for ophthalmic applications. Our system is able to write with 1 µm spot size over nearly 10 mm scan length, thereby covering $10^8$ spots per layer X-Y scan.

Figure 25:
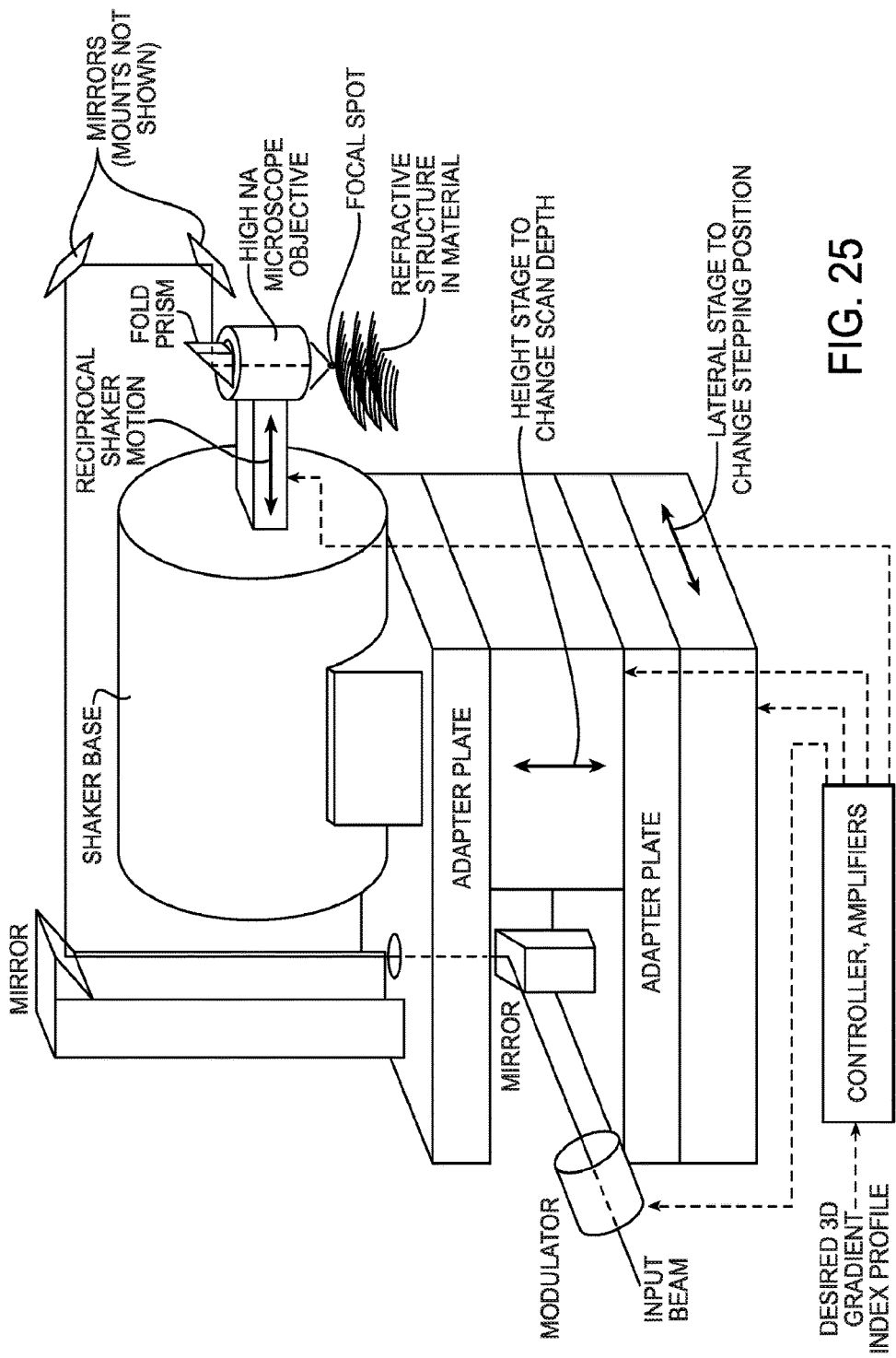
FIG. 25 shows a schematic of the prototype scanning system, including three stages.

Prototype scanning system: The prototype scanning system was designed such that the microscope objective could be scanned, rather than scanning the sample under a fixed microscope objective. This was done to demonstrate feasibility for in-vivo applications where samples cannot be moved. FIG. 25 shows a schematic diagram of one embodiment of a prototype three axis scanning system using a commercial vibration excitation stage as its high speed oscillator. The input beam is aligned and steered along each axis to ensure it enters the objective. FIG. 25 shows a schematic of the prototype scanning system, including three stages: 1) a commercial vibration exciter to provide high speed reciprocal analog translation (shaker stage), 2) a precision height stage to change the depth of the focal spot (height stage), and 3) a precision lateral translation stage aligned orthogonally to the shaker stage to provide motion in the step over direction (lateral stage).

Figure 26:
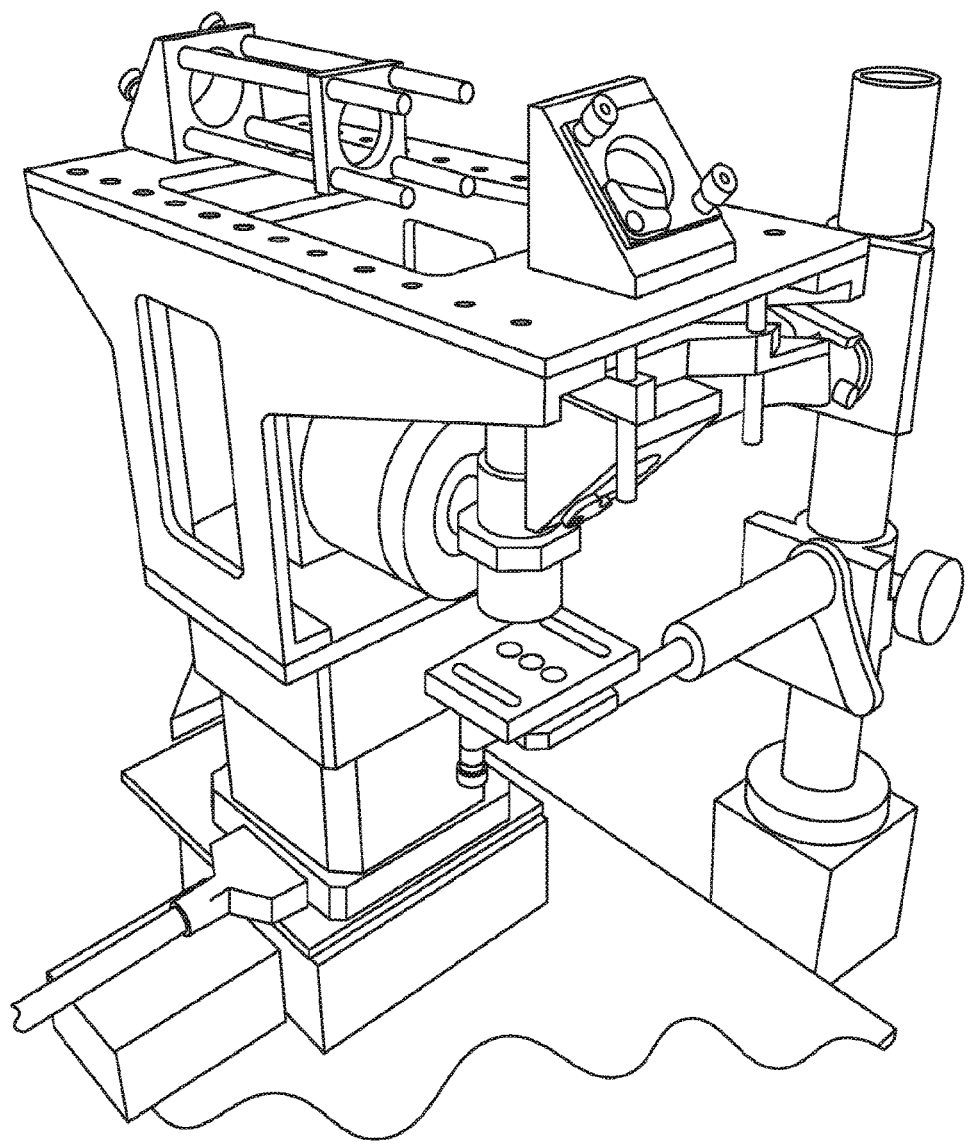
FIG. 26 shows an illustration of the prototype 3-axis scanning system a using commercial vibration exciter.

The prototype scanning system was designed around an existing commercial vibration exciter (Brüel & Kjær Measurement Exciter Type 4810) to provide high speed oscillations for an NA 1.0 water immersion microscope objective. FIG. 26 shows an illustration of the prototype 3-axis scanning system a using commercial vibration exciter. In the exemplary embodiment of FIG. 26, two separate stages are used for vertical (Newport GTS30V) and lateral motion (Newport GTS70), and a series of interface plates were machined to adapt the stages together.

Figure 27A:
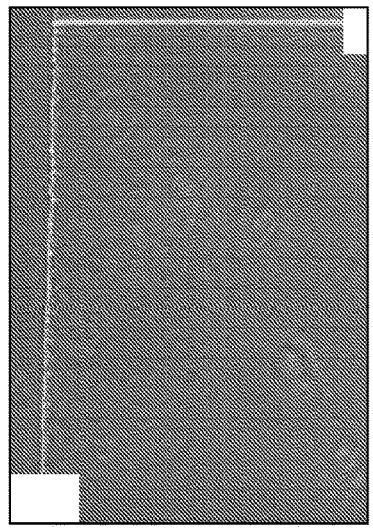
FIG. 27 shows DIC microscope photographs of RI structures written with different amplitudes using the prototype 3-axis scanning system of FIG. 25.
Figure 27B:
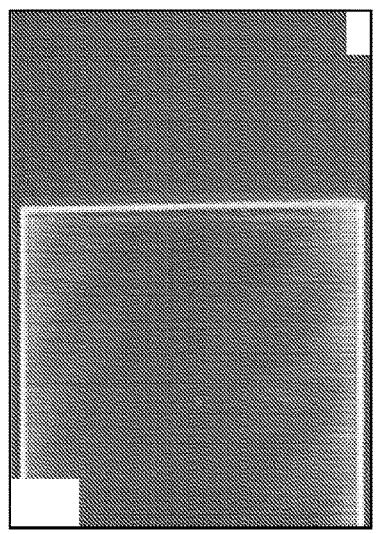

With this prototype scanning system, the translation speed profile did not contain the high frequency variations that the previous piezoelectric-drive stages exhibited, and the attainable velocities were higher. Based on the limits of the shaker stage and power amplifier used to drive it, structures could be written over a 2.5 mm wide, 10's of millimeters long area. At higher velocities, there was more variability of the end position of the written structures, which leads to the assumption that there was more variability in speed across the written profile. FIG. 27 shows DIC microscope photographs of RI structures written with different amplitudes using the prototype 3-axis scanning system of FIG. 25. Note the variability of edges at higher amplitudes/scan speeds. A) 24 mm/s in the middle at 9 Hz oscillation. B) 130 mm/s in the middle at 9 Hz. FIG. 27 shows two examples of structures written using this system in ophthalmic hydrogel polymers (used in contact lenses and intraocular lenses) exhibiting differing end conditions.

Figure 28:
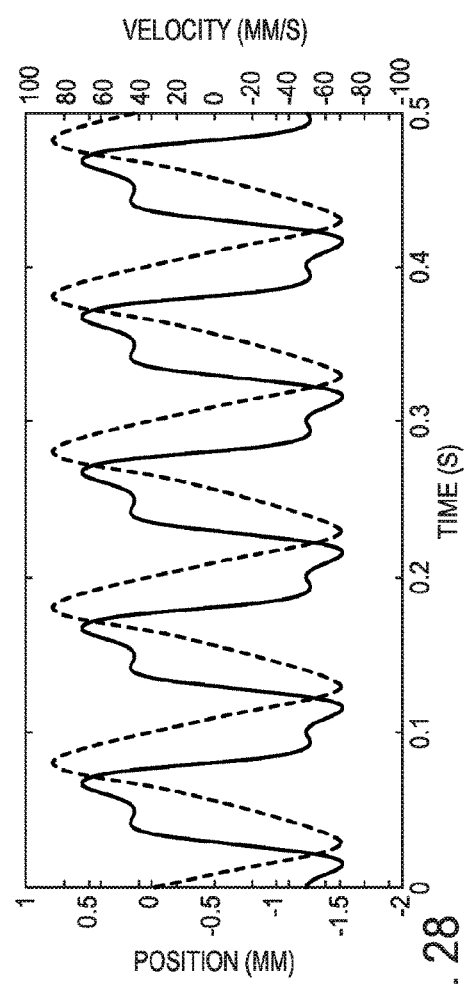
FIG. 28 shows a graph of position and velocity vs. time (a scan profile)

FIG. 28 shows a graph of position and velocity vs. time (a scan profile) for a first embodiment of a flexure scanning system with a 10 Hz oscillation. FIG. 28 shows the measured displacement and computed velocity profile of the prototype shaker stage. One suspected source of this inconsistency is the added mass on the shaker stage from the large, high NA objective. This large objective may cause a shift of higher order modes, causing them to manifest as end point deviations, changing the final position of the focal spot.

Figure 29A:
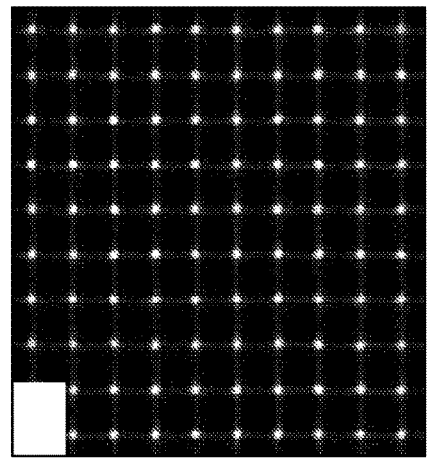
FIG. 29 shows two images from a Shack-Hartmann wavefront sensor.
Figure 29B:
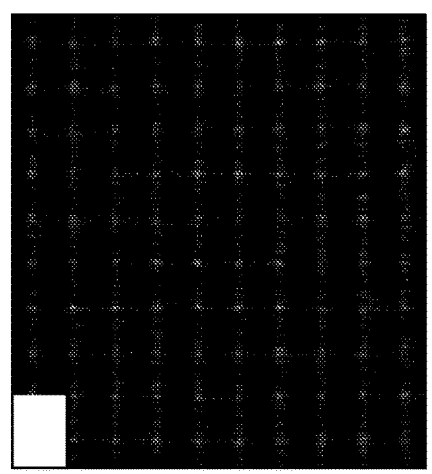

Even with these imperfections and excitation of higher order vibrational modes, as shown in FIG. 28, the velocity profile for the shaker motor is much smoother than the velocity profile of the piezoelectric stepper stages used previously (e.g. FIG. 23). While the velocity profile is no longer nominally flat, the smoother velocity profile and decrease in tracking errors leads to significantly less scattering in the measured optical wavefronts after transmission through a sample. This decrease in scattering allows these structures to be measured using a Shack-Hartmann wavefront sensor to determine the optical power of the structures. Previously, the scattering from writing using the piezoelectric stages had prevented such a quantitative assessment. FIG. 29 shows two images from a Shack-Hartmann wavefront sensor demonstrating a significant increase in image quality and reduction in scattering using the flexure type scanner as opposed to the piezo stepper stages. A) Shack-Hartmann image from structure written with stacked piezo steppers. B) Shack-Hartmann image from structure written with prototype scanning system. A comparison of the spots produced by the lenslets in the Shack-Hartmann wavefront sensor from both the piezo stepper stage and the prototype scanning system is shown in FIG. 29.

Figure 30:
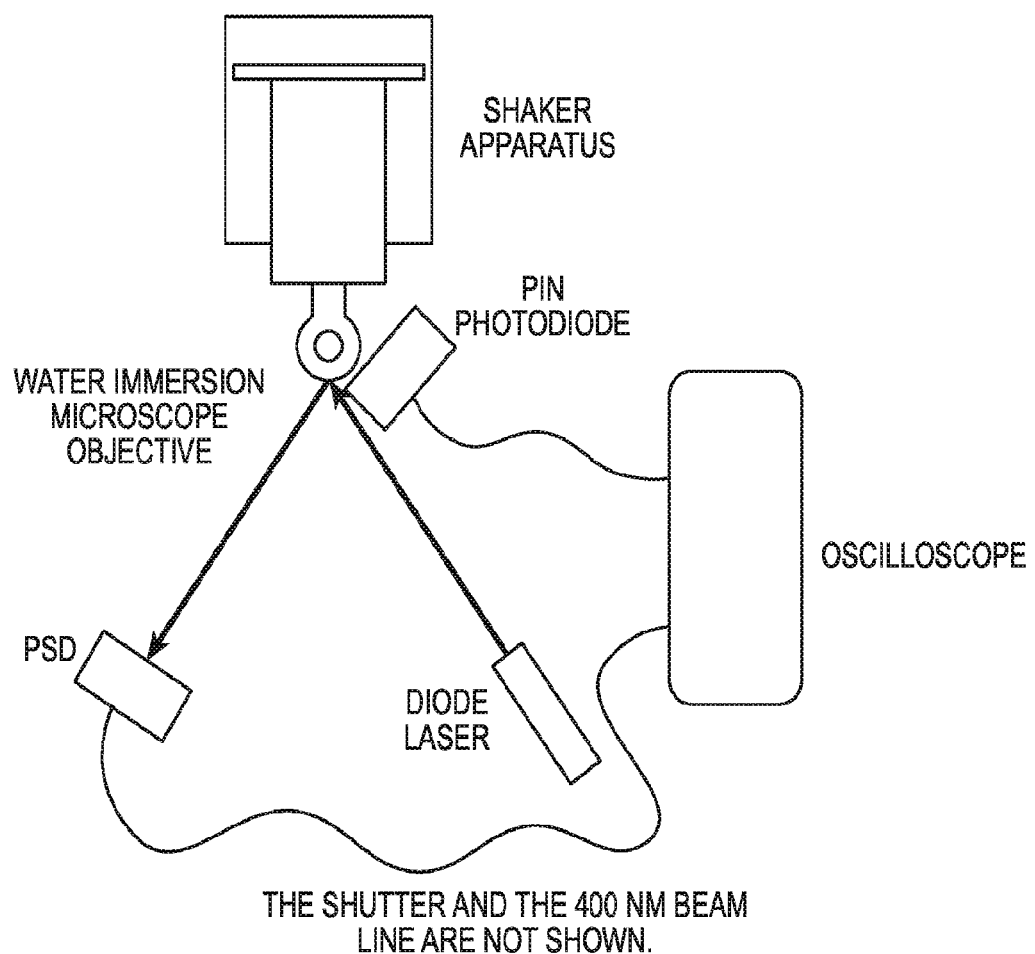
FIG. 30 shows a schematic diagram of an exemplary shutter calibration setup.

While the prototype scanning system showed significant improvement in velocity and position consistency, there were also a few inherent limitations. One problem was the zero velocity turnaround points, where the high laser power, combined with no motion, led to burns in the sample. This was a problem with the previous scanning systems as well, and was addressed here by synchronizing a high-speed mechanical shutter (Uniblitz model 214L0A0T5HB, driver model SD-10) in the path of the laser beam before it entered the 3-axis scanning system. The shutter was synchronized to the writing process by determining the relative phase lag between the shaker stage and the shutter; and determining the global phase offset relative to the shaker stage drive signal. The drive signal was recorded on an oscilloscope while a laser diode was reflected off a mirror attached to the front of the shaker stage. The reflected signal was recorded by a position sensing detector (PSD-OnTrak PSM 2-10, amplifier OT-301). FIG. 30 shows a schematic diagram of an exemplary shutter calibration setup. The PSD detected the movement of the objective while the PIN photodiode was used to determine the timing of the shutter As the shaker stage oscillates, the global phase lag between drive signal and stage motion was determined using the oscilloscope. With the global phase offset known, a PIN Photodiode (Electro-Optics Technology, Inc, ET-2000) was placed under the objective and the output intensity was recorded during oscillations, as schematically depicted in FIG. 30.

Figure 31:
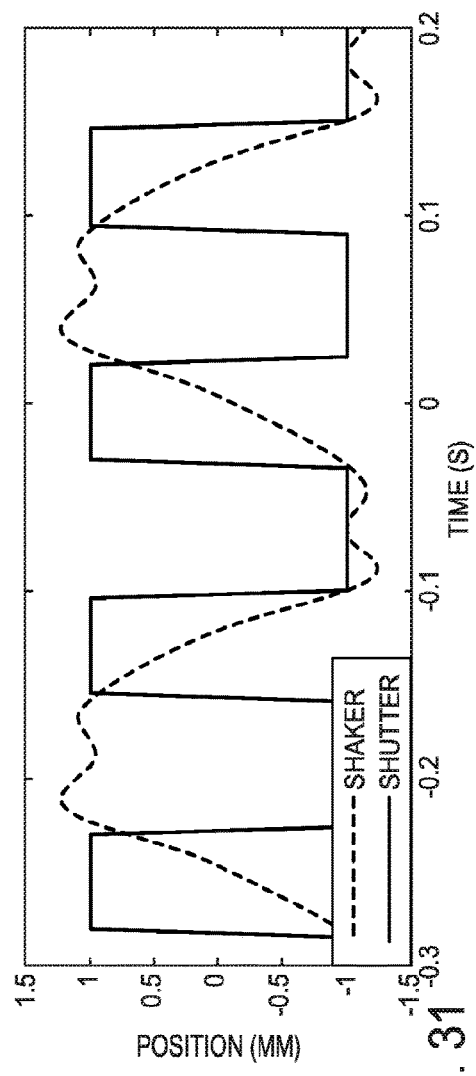
FIG. 31 shows a graph of position versus time illustrating the output of a PSD and PIN photodiode during calibration.

FIG. 31 shows a graph of position versus time illustrating the output of PSD and PIN photodiode during calibration. The noise was removed from the PIN photodiode signal to just provide an on (value of 1) or off (value of −1) signal for calibration. The shutter was then controlled by monitoring the PIN Photodiode and adjusting the phase offset on the shutter to coincide with, and to block the beam twice per revolution on the shaker stage when the velocity dropped below a specified threshold (e.g. FIG. 31. With the global phase offset and relative phase lag known, the shutter delay can be controlled outputting a shutter drive signal at twice the frequency of the shaker stage frequency with the desired offset.

The other limitations of the prototype scanning system were inherent in the design of the prototype system. The first was the stroke, which was limited to approximately 5 mm based on the shaker specifications and the amount of mass added from the microscope objective and beam steering components, even with a more powerful power amplifier (the amplifier used with this system was the limiting factor which limited it to 2.5 mm stroke). Another limitation was the low frequency response, with a resonant frequency of 16 Hz. This low frequency response limited the velocity profile control that could be achieved. Thus, a custom shaker system based on a voice coil drive with flexure guideways was designed.

Custom scanning system: Based on the performance of the vibration exciter in the prototype scanning system, we found that use of a high speed oscillator for the fast axis translation provided for smooth motion at high speeds with low higher frequency variability in the velocity profile. However, to further improve the performance from this type of scanning system, we designed a custom system.

Specifications: The following specifications were desired when building the custom system. These specifications were determined by the parameters of the micromachining process and our experience with prior scanning methods. Also, these exemplary specifications did not consider the laser source, and were only concerned with the scanning system. It is assumed that the laser will have the desired performance to write effectively and efficiently. For the structures we have previously written, we used a Spectra-Physics MaiTai HP operated at 800 nm for hydrogel writing and a Coherent Vitesse with a frequency doubler operated at 400 nm for cornea writing.

The first specification is for light focusing. For the micromachining process to work, laser light should be focused with a high NA objective [22]. This means that the custom scanning system and high speed scanning flexure must be capable of holding an objective with an NA of 0.7 in air or a 1.0 NA water immersion objective. In practice, these objectives must be interchangeable without affecting the alignment. Thus, fixed mounting hardware resulting in a defined, repeatable position is needed for the objectives.

The next specification is to minimize the time which should be used to write a structure at least 6 mm in diameter, or alternatively up to 8 mm in diameter. This is determined by the structure amplitude, the number of lines written per second, and the density of the line spacing. The prototype high speed scanning stage used 4 Hz excitation. This equates to 8 lines per second, which is too slow for practical clinical applications. In practice, each line should be up to 8 mm long, with a line spacing of 0.7 μm. Covering an 8 mm pupil diameter means that upwards of 11,500 RI lines must be written, thus the frequency of the first resonant mode must be as high as possible. It is also important that the high density lines are written with each individual line overlapping with the neighboring lines, hence the 0.7 μm line spacing specification. However, in order to minimize optical scattering from microscopic randomness in the position of the lines, the three dimensional positioning error of the focal spot should be less than 0.1 μm while scanning and optical clarity will increase with increased precision.

Figure 32:
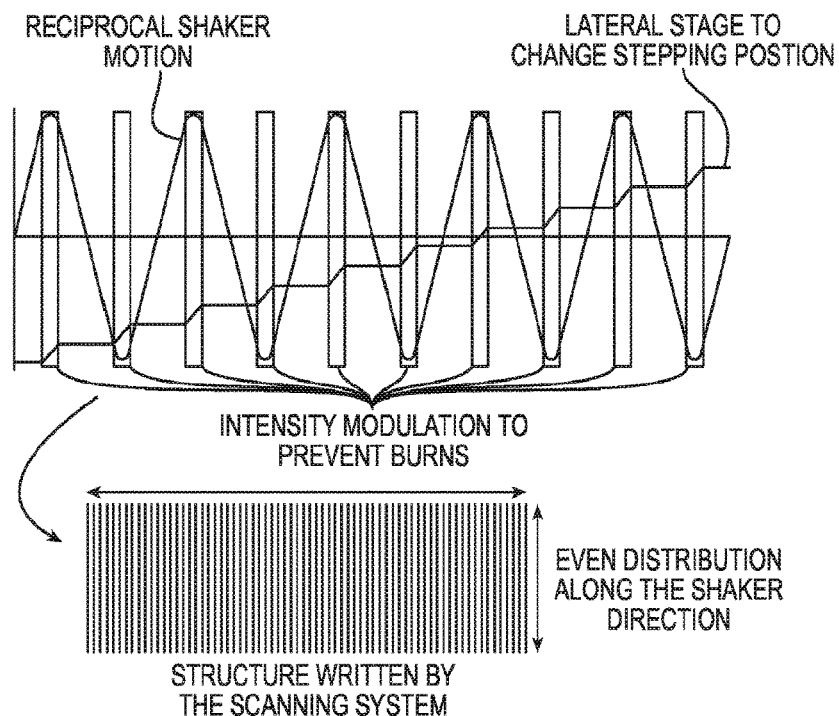
FIG. 32 shows a graph of an exemplary desired motion profile.

For quick writing, the resonant frequency should be maximized. However, in addition to writing quickly it would also be desirable to be able to control the shape of the waveform beyond a simple sinusoidal shape. FIG. 32 shows a graph of an exemplary desired motion profile. The flexure would move linearly during writing, then have parabolic turnarounds while the laser beam is blocked. The cross-axis would move over in discrete steps during the turnaround resulting in evenly spaced lines. The ideal shape of the waveform would be a linear region over which the writing occurs with parabolic turnaround sections that would be cut off using a shutter or other method of intensity control, such as an acousto-optic modulator (AOM), to prevent burning and to allow the cross-axis stage to make discrete steps (FIG. 32).

Figure 33:
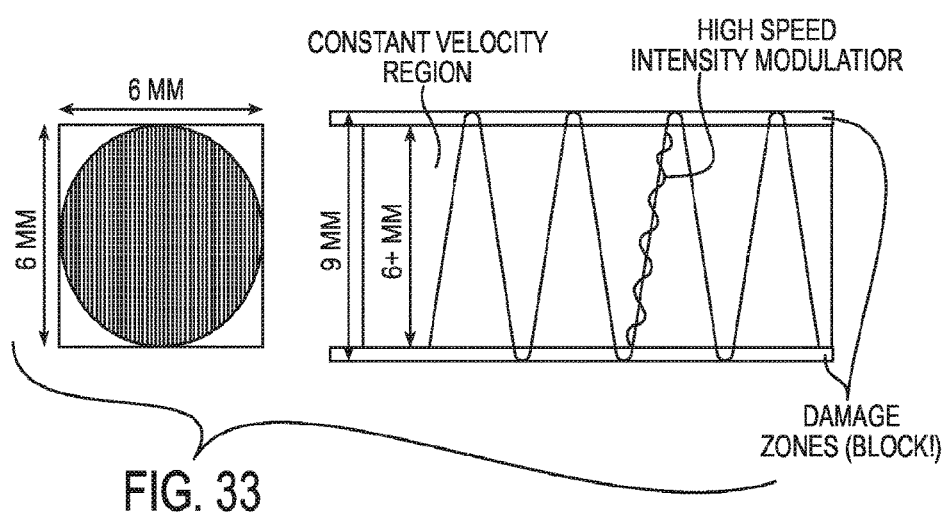
FIG. 33 shows a drawing illustrating scanning over a 6 mm diameter pupil.

Another scattering concern is the fluctuation in the index of refraction along each line. To control the fluctuation in the index of refraction along each line, the parameters that affect RI change, namely, the speed of translation of the focal spot and the intensity in the focal spot should be controllable. FIG. 33 shows a drawing illustrating scanning over a 6 mm diameter pupil where intensity modulation is used to generate the circular aperture, prevent burns, and modulate the laser power along the constant velocity section. Rather than driving the shaker stage with a sinusoidal signal, the written structure should be constant velocity during the scans, with parabolic turnaround points. FIG. 33 shows an example of writing this type of topology with the added intensity modulation.

Preliminary theoretical models suggest that fluctuations in these parameters should be minimized to ensure visual performance is not sacrificed. Along with accounting for variations in intensity and speed, intensity control also offers much better control over the shape of the index change along the lines, enabling better corrections and the ability to correct higher order aberrations. To write structures over a sufficiently large area (6-8 mm in diameter), the shaker stage range should be 8 to 9 mm, in order to compensate for the turnaround points at which the intensity must be completely blocked to prevent burning.

Design process: Based on the previous specifications and the prototype system, the architecture for the exemplary custom scanning system was centered around a high speed scanning stage that consisted of a voice coil-driven carriage to hold the microscope objective guided by flexures. Rather than using a system similar to the industrial vibration exciter, which resembles a loudspeaker, this flexure stage was designed to have a low profile, so as to simplify beam routing and manufacturing. The overall design process taken was a series of iterative steps that depended on the voice coil motors, the flexure geometry, and flexure material. Four voice coils (BEI Kimco Magnetics, model LA10-12-027A) with 1" diameter outer dimensions, 9.14 mm range, a peak force of 13.3 N, and a total mass of 70 grams each were used to drive the flexure stage. Four smaller voice coils were used instead of a single larger one to provide for a flatter profile between the coils that enables easier routing of the laser beam into the objective and more actuator force than using just two coils.

Figure 34:
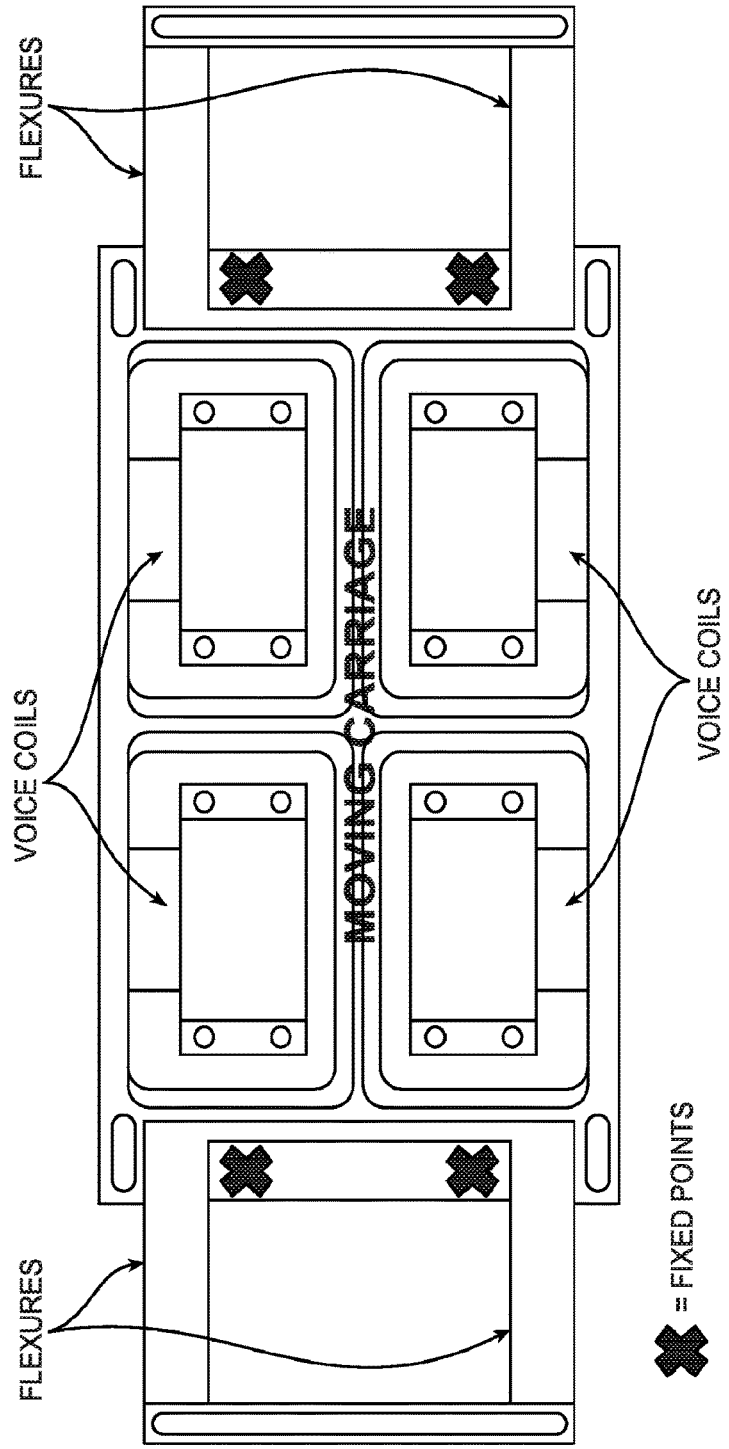
FIG. 34 shows a drawing of the initial design of an exemplary custom flexure stage with voice coils.

Because natural frequency should be maximized, the coil assembly (13.9 g per motor) was mounted to the moving carriage rather than to the field assembly (56.7 g per motor). This invariably will lead to heat dissipation issues because the coil will increase in temperature as the drive amplitude is increased, but the conduction through the flexure stage will be minimal (discussed in more detail hereinbelow). FIG. 34 shows a drawing of the initial design of an exemplary custom flexure stage with voice coils. As shown in FIG. 25, the four motors were positioned in a 2×2 configuration, attached to the central carriage of the flexure stage, with two motors pushing and two motors pulling.

A folded parallelogram flexure design was used to guide the carriage driven by the motors. This design was used to minimize the overall footprint for mounting onto the other two stages. The folded parallelogram flexures enabled a long stroke while maintaining a high stiffness to increase the natural frequency. Equation 1 was used to calculate an approximate stiffness based on an estimate of the operating force of the voice coils. Euler-Bernoulli beam theory was then used to perform first order calculations as a starting point for our design. According to Euler-Bernoulli beam theory, the equations that govern the motion, stiffness, and stress in the flexures are [29]:

$$k_{tot} = \Delta x / F_{app}, \quad (1)$$

$$k_f = \frac{12EI}{L^3}, \quad (2)$$

$$I = \frac{bt^3}{12}, \text{ and} \quad (3)$$

$$\sigma = \frac{Et\Delta x}{L^2}. \quad (4)$$

In the above equations, $k_{tot}$ is the total stiffness required, given the required range of motion. $\Delta x$, and the approximate peak force applied by the motors ($F_{app}$); $k_f$ is the stiffness in each individual flexure, E is the elastic modulus of the material, I is the second moment of area of the rectangular flexure, b is the width of the flexure, t is the thickness of the flexure, and L is the length of each flexure. Titanium (Ti6Al4V—grade 5) was selected as the material for the flexure stage because of its high tensile yield strength, which is necessary for such a large stroke. The width h was chosen as 25.4 mm, which was reasonable from a manufacturing perspective, but thick enough to push the resonant frequencies of undesired modes far beyond the desired pure translational resonant mode. The flexure thickness chosen was 0.4 mm, which after performing calculations with the above equations resulted in a required length of 30.815 mm. These dimensions resulted in a linear stiffness of 13.3 kN/m for combined flexure elements.

Figure 35:
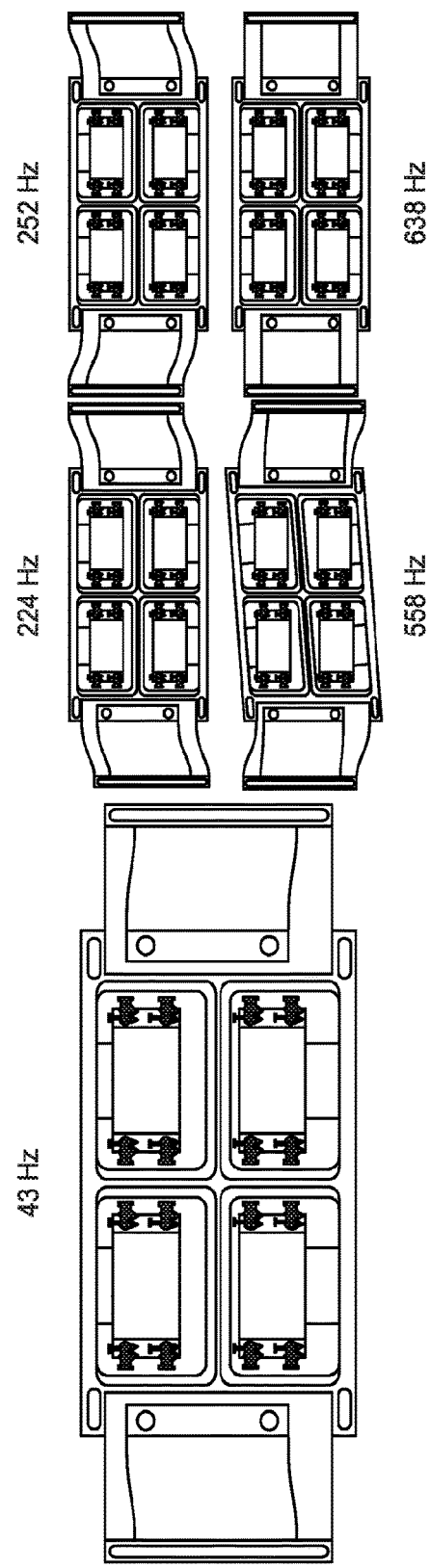
FIG. 35 shows an illustration of desired mode is shown on left with simulated natural frequency.

After calculating the required dimensions, a lightweight flexure stage was designed with four voice coil motors contained within the moving section and fabricated with wire EDM. Material was removed from all sections with unnecessary thickness to reduce the total mass as much as possible. A thin webbing was left in the center of the z-dimension in all areas where material was removed to retain rigidity. An area on the underside of the flexure carriage was left wide enough to mount a linescale. This linescale will allow for high speed position and velocity measurements of the stage, ultimately leading to closed loop control. The frequency and modes of the flexure were analyzed using the frequency analysis tool in SolidWorks. FIG. 35 shows an illustration of desired mode is shown on left with simulated natural frequency. The first five mode shapes and corresponding frequencies are shown in FIG. 35. The first four undesired modes are shown on the right. This simulation includes the mass of the flexure and moving part of the voice coils but not any fasteners, wires, or other possible sources of added mass. The natural frequencies of the undesired modes were significantly higher than the desired pure translational mode by over a factor of five (FIG. 35). This should enable the first mode to be driven without exciting the modes at higher frequencies.

Figure 36:
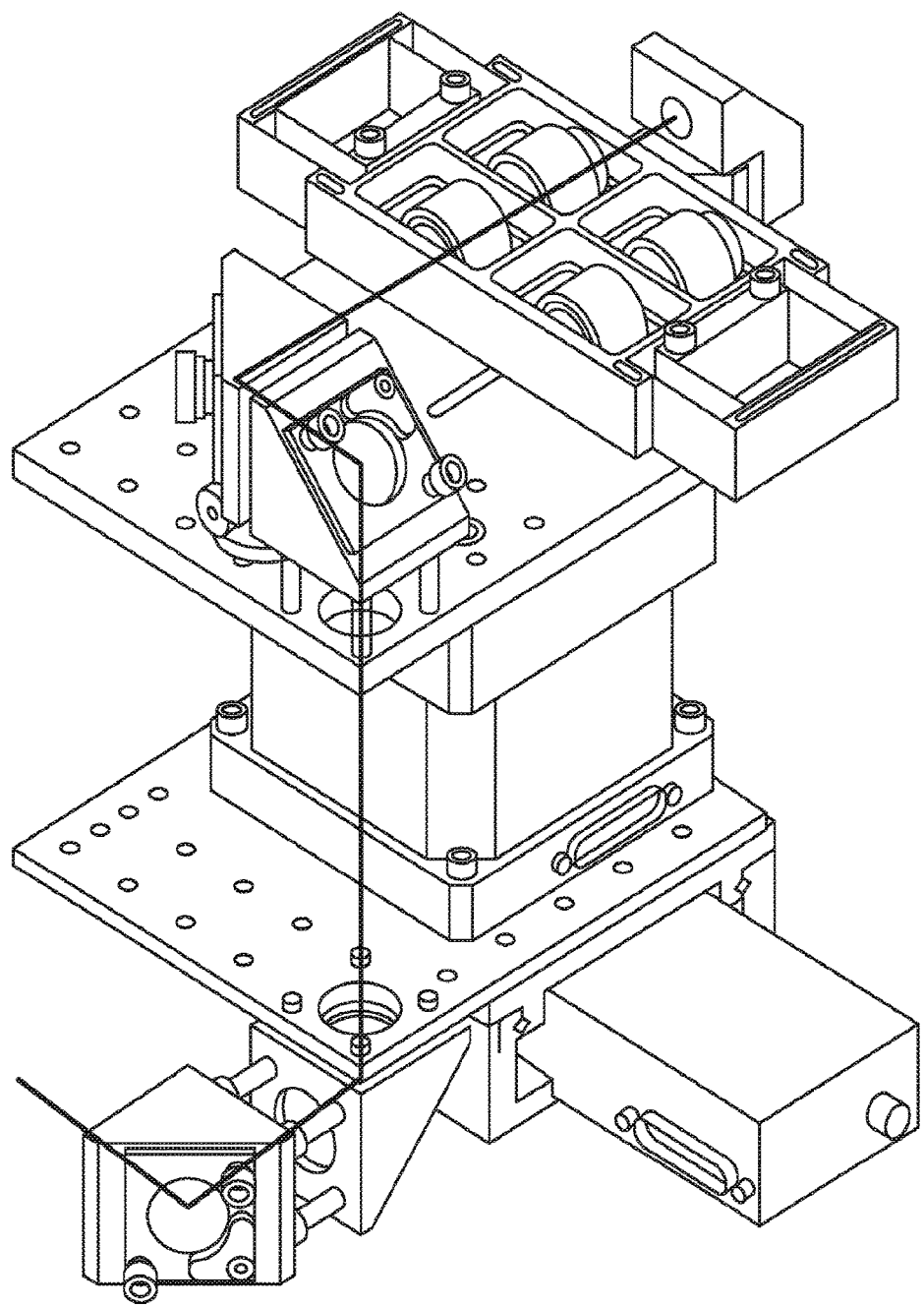
FIG. 36 shows a drawing of a CAD model of an exemplary scanning system including linear stages and steering mirrors.

FIG. 36 shows a drawing of a CAD model of an exemplary scanning system including linear stages and steering mirrors. Counterweight is not shown, but it would be attached opposite the objective as in earlier counterweight embodiments described hereinabove. Mounting plates were also designed to mount the flexure, voice coils, and mirror mounts for laser beam steering onto the vertical and horizontal linear stages. The stages selected were the same used in the first prototype flexure scanning system discussed earlier. A model of the exemplary scanning system as a whole (including linear stages and objective) is shown in FIG. 36. Each pair of mirror mounts is required to provide four degrees of freedom to align the optical axis of the laser beam to the mechanical axis of each stage. While this could lead to misalignments due to thermal expansion because of the off-center location of the mounts, we expect this effect to be negligible in our system.

Intensity control: Custom refractive structures can be written into ophthalmic materials by varying the RI across a 3-dimensional region using a focused laser. The index change created in the focal point can be quantitatively modeled as a function of the focal point velocity and intensity of the laser source. Intensity control is a better variable than velocity for rapidly and predictably modulating index. In this exemplary embodiment, an acousto-optic modulator (AOM) was used due to its rapid rise time (on the order of 100 ns/mm beam waist). Specifically, the system uses the Isomet M1133-aQ80L-1.5 AOM with an Isomet 532C-7 driver.

The AOM modulates intensity by diffracting an amount of light proportional to the acoustic wave amplitude into the first diffraction order. The percentage of incident light deposited into the first diffraction order is known as the diffraction efficiency. The Isomet AOM achieved a peak diffraction efficiency of about 72% after focusing the beam into the glass, centering this focal point in the glass, setting the proper Bragg angle, aligning the glass to the polarization of the laser, and tuning the driver power. Thus the intensity striking the target can be modulated between about 0% and about 72% of the source's base intensity.

A quantitative relationship was established between the voltage supplied to the AOM driver and the diffraction efficiency of the AOM. This relationship was highly non-linear and was fit using a high-order polynomial. In one exemplary embodiment, the scanning setup is driven using Mathworks Simulink models running on the xPC Target Real-time Operating System (RTOS). This system contains an intensity control algorithm that continuously queries the current position of the focal point on the target and determines the AOM input voltage required to create the desired index change in that location. From the input position, the algorithm computes the current focal spot velocity using differentiation or a pre-determined velocity profile. The user provides the algorithm with a desired RI change as a function of position. The quantitative index change model is then used to determine the incident laser intensity required to create the desired index change at the current velocity. After correcting for static system loss, the required intensity is divided by the measured base laser power entering the system to determine the open loop diffraction efficiency required from the AOM. Using the characterization curve described above, the voltage sent to the AOM driver can be determined from the required diffraction efficiency.

Figure 37:
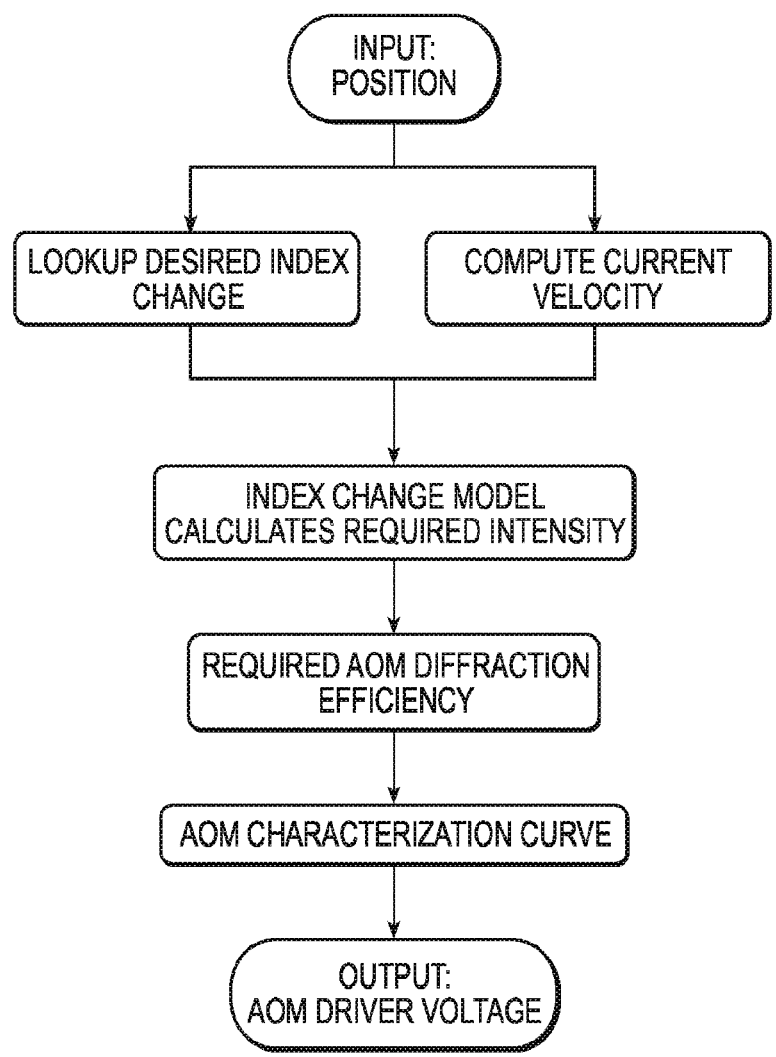
FIG. 37 shows a flowchart of an exemplary process algorithm.

FIG. 37 shows a flowchart of an exemplary process algorithm that can be run on a computer to determine the voltage at which to drive the AOM based on the position of the stage, the desired RI at that position, and the current velocity of the objective.

The method used for querying the current position of the focal point is dependent on the mechanical scanning system used. Currently, this method of intensity control has been tested on the PILine Piezo stepper system. In this case, the current position of the stages was queried from the motor controllers. Although this served as a proof of concept, this method was limited to sampling the position at about 167 Hz due to limitations in the querying response of the motor controllers. In the new custom scanning system, a linescale will be able to query the position of the fast-axis at a rate of at least 7 kHz and potentially higher, based on our custom FPGA-based data acquisition and real-time Ethernet controller [30]. At the current maximum velocity that structures are written at (50 mm/s) this would result in a less than 10 μm error along the line. As the maximum velocity is increased, the control scheme will likely be reevaluated and improved, but this error is acceptable for the current research.

DMI TESTING, Experimental setup: FIG. 38 shows a schematic of an exemplary interferometer that was used for measurement from Refs. [31, 32]. The flexure stage was calibrated using a custom heterodyne interferometer configuration of FIG. 16 that used a small profile beam to reflect from a mirror epoxied to the stage [31, 32]. This configuration was used over other traditional interferometer configurations because the small beam profile and small mirror (Ø7 mm, 2 mm thick) had minimal impact for measuring the natural frequency of the stage. The heterodyne frequency was set at about 5 MHz by driving two different acousto-optic modulators at about 80 MHz and 85 MHz. The measurement and reference signals in the interferometer were detected with two commercial photodiodes (Thorlabs, PDA36A) with 10 MHz bandwidth. The detected measurement and reference signals from the displacement interferometer were converted to digital representations using A/D 14-bit daughter cards (Terasic Technologies, High Speed AD/DA Card) and processed using a custom single-bin discrete Fourier transform (SBDFT) process algorithm implemented in a FGPA demonstration board (Terasic Technologies, Altera DE2 board).

FIG. 39 shows a block diagram of an exemplary process algorithm used to analyze the signal received from the interferometer. The exemplary SBDFT process algorithm used board generated in-phase and quadrature signals which were multiplied with the measurement and reference beams respectively, as shown in FIG. 39. These signals were filtered and the arctangent was computed to determine the phase of the measurement and reference signals. The phases were then unwrapped and subtracted to extract the relative phase between the reference and measurement signals and remove common spurious noise effects before being converted to displacement, which has a static resolution as fine as ±18 μm depending on the velocity and settings chosen [30]. Based on the filters and other settings, the displacement of a moving target could be measured with velocities up to ~630 mm/s which correspond to Doppler frequency shifts of ~2 MHz, which is sufficient for the present application, but could be increased. The measured phase was then recorded using Ethernet user datagram protocol (UDP) transmitted to an xPC-target computer system (Mathworks™) for logging the data and further processing.

Figure 40:
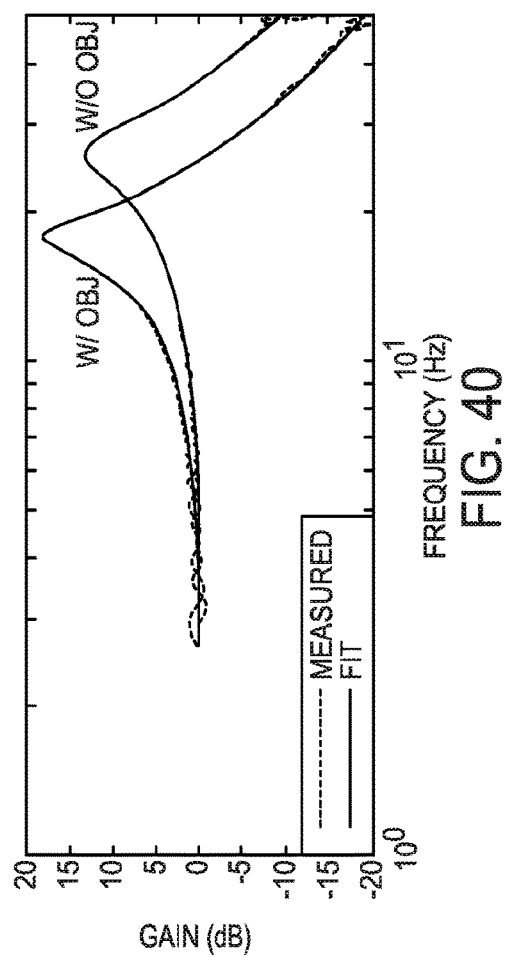
FIG. 40 shows a graph of Gain versus frequency of measured and fit gain curves for both with and without the objective attached.

Results: Using the displacement measuring interferometry system described in the previous section, multiple measurements were made of the final flexure, both with and without an objective attached. The first measurement performed in each case was of the vibration spectrum. For this measurement, the function generator was set to output a linearly chirped sine wave from 1 Hz to 50 Hz over 30 seconds. This was performed at multiple output voltages to determine the linearity of the gain with respect to maximum amplitude. The DMI measurement data was Fourier transformed using MATLAB™ and normalized to the low frequency signal. The flexure acts as a simple mass-spring-damper system which has a gain curve governed by [21].

$$|H(\omega)| = \frac{1}{k} \frac{1}{(1 - \omega^2/\omega_n^2) + (2\zeta\omega/\omega_n)^2}, \quad (5)$$

where $H(\omega)$ is the amplitude gain, k is the stiffness, $\xi$ is the damping ratio, w is the driving angular frequency, and $\omega_n$ is the natural frequency. A fit was found for each curve using Equation 5 to determine the natural frequency and damping ratio. The values obtained from the fit are shown in Table I. Sample vibration spectra are shown in FIG. 39 for both with and without the objective and counterweight attached. FIG. 40 shows a graph of Gain versus frequency of measured and fit gain curves for both with and without the objective attached. The curve with the lower natural frequency is with the objective; the other is without. The oscillations at 50 Hz are an artifact of the Fourier Transform used to calculate the gain for the swept sine wave and the fact that the swept sine ends at 50 Hz, similar to the oscillations at the low frequencies.

Table I shows a comparison of natural frequency and damping ratio between flexure with and without objective and counterweight attached:

| | Without Objective | | With Objective | |
|---|---|---|---|---|
| V (mV) | $f_n$ (Hz) | $\xi$ | $f_n$ (Hz) | $\xi$ |
| 10 | 26.61 | 0.134 | 18.05 | 0.0807 |
| 20 | 26.58 | 0.136 | 18.02 | 0.0802 |
| 50 | 26.55 | 0.135 | 18.00 | 0.0800 |
| 100 | 26.54 | 0.138 | 17.97 | 0.0802 |
| 200 | 26.48 | 0.139 | 18.07 | 0.0811 |
| average | 26.55 | 0.136 | 18.02 | 0.0804 |
| standard deviation | 0.05 | 0.002 | 0.04 | 0.0005 |

An Olympus LUCPlanFLN 60×/0.70NA objective mounted to the front of the flexure was used for this measurement. The objective and aluminum objective mount together had a mass of 241 g, not including the screws used for mounting to the flexure. The counterweight attached to the back of the flexure was sized to be the same mass as the objective and objective mount together. This counterweight was used to limit exciting the unwanted resonant modes. The actual mass of the counterweight was approximately 232 g, not including the fasteners used to attach it to the flexure carriage.

Figure 41:
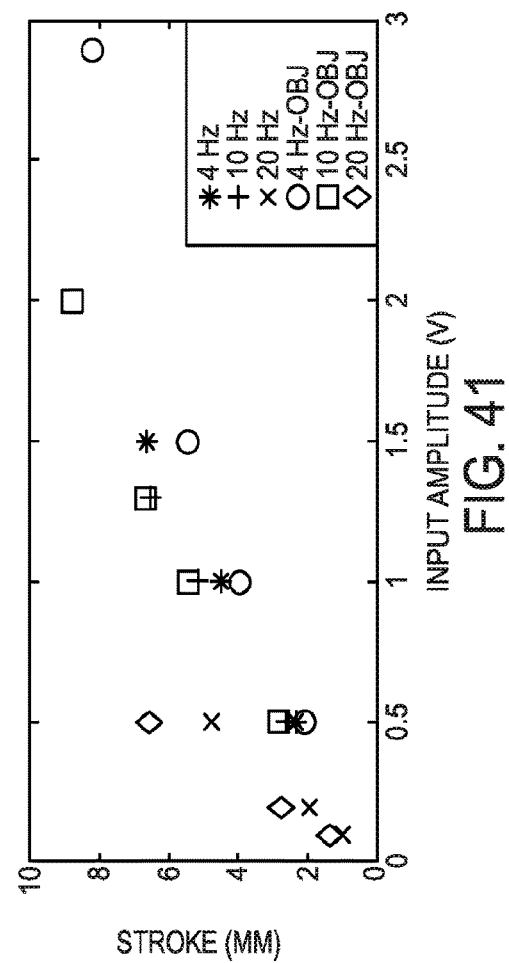
FIG. 41 shows a plot of stroke versus input amplitude of achieved stroke at different frequencies and input voltages.

After the vibration spectra were recorded, the flexure was tested with sinusoidal inputs at different amplitudes and frequencies to observe the resulting waveform and velocity profile. The frequencies that were tested were 4 Hz, 10 Hz, and 20 Hz. During these measurements, the maximum stroke achieved was 8.75 mm. This exceeded the desired stroke of 8 mm set out earlier in this paper. FIG. 41 shows a plot of stroke versus input amplitude of achieved stroke at different frequencies and input voltages. The stroke appears to be linear with stroke up to approximately 6 mm, becoming nonlinear at larger strokes possibly from the actuator coil partially leaving the magnetic field. The increase in stroke with voltage was approximately linear at lower voltages but became nonlinear at higher voltages as shown in FIG. 41.

Figure 42C:
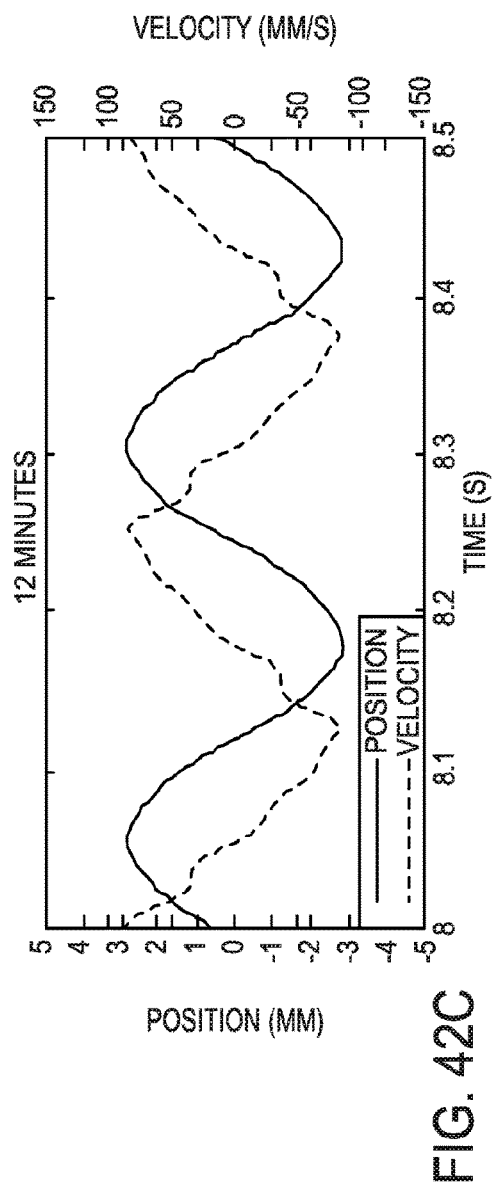
FIG. 42C shows a graph of position and velocity versus time at 12 minutes.
Figure 42D:
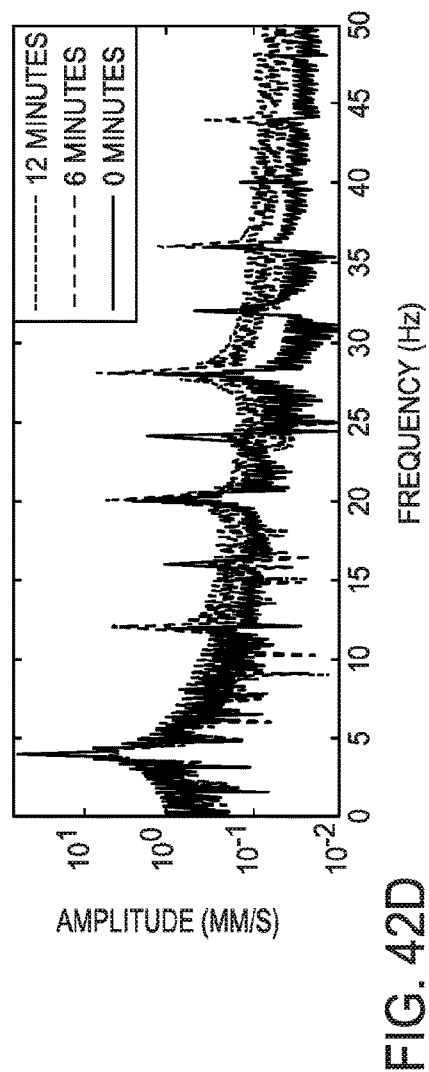
FIG. 42D shows a graph of spectral graph of amplitude versus frequency at 0, 6, and 12 minutes.

It was observed that the waveform at higher input amplitudes evolved in time with the odd order higher harmonics gradually growing. FIG. 42A, FIG. 42B, FIG. 42C, and FIG. 42D show the time evolution of 4 Hz waveform with a 1.5 V sinusoidal input with the corresponding Fourier transforms of the velocity curves. FIG. 42A shows a graph of position and velocity versus time at 0 minutes. FIG. 42B shows a graph of position and velocity versus time at 6 minutes. FIG. 42C shows a graph of position and velocity versus time at 12 minutes. FIG. 42D shows a graph of spectral graph of amplitude versus frequency at 0, 6, and 12 minutes.

As the voice coils increase in temperature from use, the odd order higher harmonics grow significantly. The time evolution a sample waveform without the objective attached is shown in FIG. 42D along with the corresponding Fourier series decompositions of the velocities. The evolution of the waveform appears to stabilize after 12 minutes for most drive amplitudes.

This evolution of the waveform is likely due to thermal issues related to the heat generated by the voice coils at higher input amplitudes and longer operation times. Another result of the heat in the flexure was a decrease in maximum range as a function of time. This was seen regardless of what input amplitude was chosen.

Figure 43:
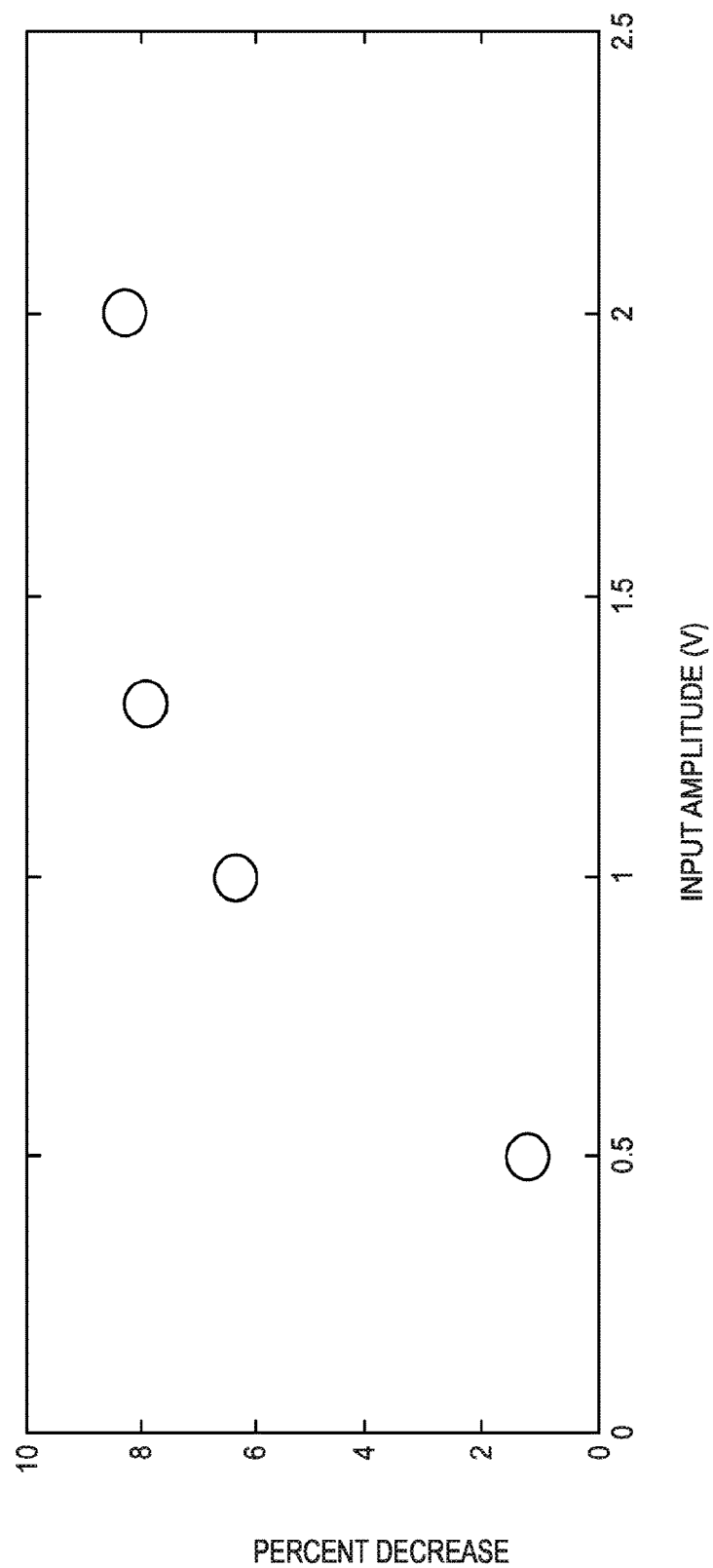
FIG. 43 shows a graph of percent decrease in the stroke versus input amplitude.

FIG. 43 shows a graph of percent decrease in the stroke versus input amplitude. Percent decrease in the stroke of the flexure at different input amplitudes. The data points were calculated as the difference between the stroke shortly after starting the flexure at room temperature and the stroke after 15 minutes of continuous operation. This difference was compared to the initial stroke to get the percentage. The percent loss in output amplitude for a 10 Hz input at different input amplitudes is shown in FIG. 43. This frequency was chosen because the third harmonic does not appear because it is sufficiently above the resonance and is significantly attenuated, resulting in a sinusoidal waveform at all input voltages. The percent difference was calculated between 0 minutes and 15 minutes.

Discussion: The measured natural frequency of the flexure alone was lower than expected. This is likely from additional masses not included in the initial modeling of the flexure stage, including fasteners and the linescale. While lower than expected, the natural frequency with the objective was still approximately the same as the first prototype built using the commercial vibration exciter, thus there has been no decrease in frequency performance with the custom scanning system. However, the range of the new scanning system was approximately four times greater than that of the prototype commercial exciter, which is sufficient for the great majority of clinical ophthalmic applications. It should also be possible to further increase the natural frequency of the operating system by designing a custom high NA objective. Current objectives used for microscopy, like the one used in our experiments, have multiple features that are unnecessary for our purposes, such as chromatic correction over the entire visible spectrum and field correction to form images. By designing a lens system optimized just for approximately a 20 nm wavelength band around the laser wavelength (to account for the wavelength broadening of the femtosecond pulses) and only on axis with a little bit of leeway for alignment, the mass of the objective could be reduced significantly, which would bring the frequency performance closer to that of the flexure alone.

The heating of the flexure could be a larger problem however, because it limits the frequencies and maximum stroke attainable, and because of the possibility of heat-induced damage to the coils. As described hereinabove, the coils were mounted to the moving carriage of the flexure stage to reduce the overall payload. This reduced the moving mass due to the motors by four times over moving the field assembly of the motors, but can lead to significant heat generation through the coils. The large amount of heat generated could lead to thermal distortion of the moving carriage and flexure bearings. This distortion would likely cause a thermal stress on the flexures, with a compressive load on the outer flexures and a tensile load on the inner flexures. This could be a possible cause of the observed temporal growth of the higher order harmonics. At lower input amplitudes (<500 mV), the waveform of the flexure remained sinusoidal. Only the odd harmonics were excited, so increasing the frequency to the point where the $3^{rd}$ harmonic is sufficiently attenuated would also eliminate the excitation of the higher harmonics. While this problem is reduced at higher frequencies, when the stage is driven near resonance, the stage's waveform cannot be controlled as well at higher frequencies, which is undesirable.

In future embodiments, the flexure elements could be more thermally isolated from the coils by either insulating the coils from the moving carriage with a low conductivity material or increasing the distance between the coils and the flexure. However, a concern with attaching the coils to a low conductivity material would be heat buildup in the coils leading to damage. The design decision to mount the coils to the flexure can also be reexamined to determine if the thermal instability is enough of a problem that it is worth sacrificing a higher frequency response by mounting the field assembly to the moving carriage instead. One option for reducing this effect in the current system may be to add an air circulation system to enhance heat dissipation. Increased convection would allow for higher drive voltages and higher drive frequencies with less stroke loss, although one should also consider that with added circulation, come potential RI fluctuations from the air motion due to possible distortions of the laser beam profile from the air currents. Another option is to provide cooling via heat pipes that have forced area or conductive cooling.

CONCLUSIONS

We described hereinabove an exemplary scanning system and a new custom scanning system for performing localized, femtosecond micromachining of ophthalmic materials over a lame field. Both scanning systems were designed to route the beam path through a three-axis system, ensuring that the sample could remain stationary during the operation for in-vivo studies.

The prototype scanning system was capable of micromachining structures over a 2.5 mm field, suitable to perform preliminary experiments. Using this prototype system, we demonstrated that structures with high visual quality could be written in ophthalmic hydrogels and in-vivo cat cornea [33]. Additionally, we designed a system for measuring and synchronizing a shutter to block the input beam at the turnaround points, thus preventing damage to the sample.

Using the prototype system as a basis for a custom scanning stage, a long range, high speed flexure stage was designed to cover a >8 mm field while carrying a NA=1.0 water immersion microscope objective. We demonstrated this design to possess a 4× improvement in range over the above-mentioned prototype system, while maintaining a similar natural frequency. We believe this design to be highly promising as a new scanning system for the IRIS process and will enable significant advancement of our understanding and development of IRIS as a clinical refractive correction tool.

The new high numerical aperture optomechanical scanner for layered gradient index microlenses, methods, and applications described hereinabove can make use of any suitable techniques for writing refractive index changes. Exemplary suitable methods and techniques have been described, for example, in U.S. Pat. No. 7,789,910 B2, OPTICAL MATERIAL AND METHOD FOR MODIFYING THE REFRACTIVE INDEX, to Knox, et. al.; U.S. Pat. No. 8,337,553 B2, OPTICAL MATERIAL AND METHOD FOR MODIFYING THE REFRACTIVE INDEX, to Knox, et. al.; U.S. Pat. No. 8,486,055 B2, METHOD FOR MODIFYING THE REFRACTIVE INDEX OF OCULAR TISSUES, to Knox, et. al.; U.S. Pat. No. 8,512,320 B1, METHOD FOR MODIFYING THE REFRACTIVE INDEX OF OCULAR TISSUES, to Knox, et. al.; and U.S. Pat. No. 8,617,147 B2, METHOD FOR MODIFYING THE REFRACTIVE INDEX OF OCULAR TISSUES. All of the above named patents, including the '910, '553, '055, '320, and '147 patents are incorporated herein by reference in their entirety for all purposes.

Software and/or firmware for a high numerical aperture opto-mechanical scanner for writing refractive index modifications is typically provided on a computer readable non-transitory storage medium as non-transitory data storage. A computer readable non-transitory storage medium as non-transitory data storage includes any data stored on any suitable media in a non-fleeting manner. Such data storage includes any suitable computer readable non-transitory storage medium, including, but not limited to hard drives, non-volatile RAM, SSD devices, CDs, DVDs, etc.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompassed by the following claims.

REFERENCES

[1] "Large refractive index change in silicone-based and non-silicone-based hydrogel polymers induced by femtosecond laser micro-machining," Ding L, Blackwell R, Künzler J f, Knox W H. Optics Express 2006; 14:11901-11909, and U.S. Pat. No. 7,789,910, "Optical material and method for modifying the refractive index," W. H. Knox, L. Ding, J. F. Kunzler, D. Jani, C. D. Pinto.

[2] "Intratissue Refractive Index Shaping (IRIS) of the cornea and lens using a low-pulse-energy femtosecond laser oscillator," Ding L, Knox W H, Bühren J, Nagy L J, Huxlin K R. Investigative Ophthalmology and Visual Science 2008; 49:5332-5339, "Potentiation of femtosecond laser Intratissue Refractive Index Shaping (IRIS) in the living cornea with sodium fluorescein," Nagy L J, Ding L, Xu L, Knox W H, Huxlin K R. Investigative Ophthalmology and Visual Science 2010; 51:850-856.

[3] "Lateral gradient index microlenses written in ophthalmic hydrogel polymers by femtosecond laser micromachining," Xu, Lisen; Knox, Wayne H, Optical Materials Express, Vol. 1 Issue 8, pp. 1416-1424 (2011)

[4] "Fiber-coupled 3-DOF interferometer for EUV lithography stage metrology," Ellis J D, Gillmer S, Wang C, Smith R, Woody S C, Tarbutton J, y, in: Proceedings of ASPE Summer Topical Meeting: Precision Engineering and Mechatronics Supporting the Semiconductor industry, 24-26 Jun. 2012, Berkeley, Calif., USA and US Provisional Patent Application 176/900100 "Interferometer, system, and method of use" J. D. Ellis and J. W. Spronck

[5] "Miniature, fiber-coupled 3-DOF interferometer for precision micro-motion stage metrology," Gilimer S R, Smith R G C, Woody S C, Tarbutton J, Ellis J D. In: Proceedings of the 27th ASPE Annual Meeting, 21-26 Oct. 2012, San Diego, Calif., USA

[6] "Interferometer, System, and Method of Use," Ellis J D and Spronck J W, PCT Patent Application 176-900101

[7] "Effectively single-mode all-solid photonic bandgap fiber with large effective area and low bending loss for compact high-power all-fiber lasers," Masahiro Kashiwagi, Kunimasa Saitoh, Katsuhiro Takenaga, Shoji Tanigawa, Shoichiro Matsuo, and Munehisa Fujimaki, Optics Express Volume 20 Issue 14 Page 15061 (2012)

[8] "Fast voice-coil scanning optical-resolution photoacoustic microscopy," Lidai Wang, Konstantin Maslov, Junjie Yao, Bin Rao, and Lihong V. Wang, Jan. 15, 2011/Vol. 36, No. 2/OPTICS LETTERS There is a need for an.

[9] W. J. Smith, Modern Optical Engineering (McGraw-Hill, New York, 2008)

[10] K. Minoshima, A. M. Kowalevicz, I. Hartl, E. P. Ippen, and J. G. Fujimoto, Optics Letters, 26, 1516 (2001).

[11] K. Minoshima, A. M. Kowalevicz, E. P. Ippen, and J. G. Fujimoto, Optics Express, 10, 645 (2002).

[12] K. M. Davis, K. Miura, N. Sugimoto, and K. Hirao, Optics Letters, 21, 1729 (1996).

[13] N. Takeshima, Y. Kuroiwa, Y. Narita, S. Tanaka, and K. Hirao, Optics Express, 12, 4019 (2004).

[14] N. Takeshima, Y. Narita, S. Tanaka, Y. Kuroiwa, and K. Hirao, Optics Letters, 30, 352 (2005).

[15] R. Osellame, N. Chiodo, G. D. Valle, S. Taccheo, R. Ramponi, G. Cerullo, A. Killi, U. Morgner, M. Lederer, and D. Kopf, Optics Letters, 29, 1900 (2004).

[16] C. B. Schaffer, A. Brodeur, J. F. Garcia, and E. Mazur, Optics Letters, 26, 93 (2001).

[17] A. M. Streltsov, and N. F. Borrelli, Optics Letters, 26, 42 (2001).

[18] Alexander M. Streltsov, and Nicholas F. Borrelli, J. Opt. Soc. Am. B. 19, 2496 (2002).

[19] E. N. Glezer, M. Milosavljevic, L. Huang, R. J. Finlay, T. H. Her, J. P. Callan, and E. Mazur, Optics letters, 21, 2023 (1996).

[20] Y. Nasu, M. Kohtoku, and Y. Hibino, Optics Letters, 30, 723 (2005).
[21] L. Ding, R. Blackwell, J. Kunzler, W. Knox, Optics Express, 14, 11901 (2006.
[22] L. Xu, Ph.D Thesis, University of Rochester, Rochester, N.Y., 2013
[23] L. Ding, D. Jani, J. Linhardt, J. F. Kiinzler, S. Pawar, G. Labenski, T. Smith, and W. H. Knox, Optics Express, 16, 21914 (2008).
[24] L. Xu, W. Knox, Optical Materials Express, 1, 1416 (2011)
[25] L. Ding, J. Bühren, L. J. Nagy, W. H. Knox, and K. R. Huxlin, Investigative Ophthalmology and Vision Science, 49, 5332 (2008).
[26] L. J. Nagy, L. Ding., L. Xu, W. H. Knox, and K. R. Huxlin, Investigative Ophthalmology and Vision Science, 51(2), 850 (2010).
[27] L. Xu, W. Knox, M. DeMagistris, N. Wang, K. Huxlin. Noninvasive Intratissue Refractive Index Shaping (IRIS) of the Cornea with Blue Femtosecond Laser Light. IOVS. 2011; 52: 8148-8155; published ahead of print Sep. 19, 2011, doi:10.1167/iovs.11-7323.
[28] D. R. Brooks, N. S. Brown, L. Xu, D. E. Savage, W. H. Knox, and J. E. Ellis, In: Proceedings of the 28th ASPE Annual Meeting, 20-25 Oct. 2013, St. Paul, Minn., USA
[29] S. T. Smith, Flexures: Elements of Elastic Mechanisms (CRC Press, New York, 2000)
[30] C. Wang, Master's Thesis, University of Rochester, Rochester, N.Y., 2013
[31] J. D. Ellis, S. R. Gillmer, C. Wang, R. G. C. Smith, S. C. Woody, In: Proceedings of ASPE Summer Topical Meeting: Precision Engineering and Mechatronics Supporting the Semiconductor Industry, 24-26 Jun. 2012, Berkeley, Calif., USA
[32] S. R. Gillmer, R. G. C. Smith, S. C. Woody, J. Tarbutton, J. D. Ellis, In: Proceedings of the 27th ASPE Annual Meeting, 21-26 Oct. 2012, San Diego, Calif., USA

What is claimed is:

1. A high numerical aperture opto-mechanical scanner for writing refractive index modifications comprising:
    a fast axis scanner having a fast scanning axis, said fast axis scanner comprising a moving carriage which defines a carriage x-y plane, said moving carriage movable in or parallel to said carriage x-y plane, along said fast scanning axis;
    a waveform generator electrically coupled to said fast axis scanner, and a waveform provided by said waveform generator which substantially defines a fast scan motion profile of said fast axis scanner;
    a scanning lens assembly mechanically coupled to said fast axis scanner, said scanning lens assembly having a NA greater than about 0.5 and a scanning lens motion along said fast scanning axis; and
    a femtosecond laser optically coupled through said scanning lens assembly to a surface of a material, creating a femtosecond laser light scanning pattern to write said refractive index modifications into said material.

2. The high numerical aperture opto-mechanical scanner of claim 1, wherein said material comprises a cornea of an animal or human eye.

3. The high numerical aperture opto-mechanical scanner of claim 1, wherein said material comprises a hydrogel.

4. The high numerical aperture opto-mechanical scanner of claim 1, wherein said waveform comprises an arbitrary waveform or a sine wave.

5. The high numerical aperture opto-mechanical scanner of claim 1, further comprising a modulator disposed between said laser and said material.

6. The high numerical aperture opto-mechanical scanner of claim 1, wherein said fast axis scanner further comprises a balancing mass that substantially matches a scanning lens assembly mass.

7. The high numerical aperture opto-mechanical scanner of claim 1, wherein said fast axis scanner and said scanning lens assembly is mounted on a slow scanning stage having a slow scan motion axis substantially orthogonal to said fast scanning axis.

8. The high numerical aperture opto-mechanical scanner of claim 7, further comprising a rotation stage.

9. The high numerical aperture opto-mechanical scanner of claim 8, further comprising a z-axis scanner having an axis substantially orthogonal to both said fast scanning axis and said slow scan motion axis.

10. The high numerical aperture opto-mechanical scanner of claim 1, wherein said scanning lens assembly comprises a depth control stage or a spherical aberration correction stage.

11. The high numerical aperture opto-mechanical scanner of claim 1, further comprising an optical sensor that provides a measurement selected from the group consisting of displacement, straightness, pitch, yaw and roll of the scanning lens assembly to correct a position of the scanning lens assembly during scanning.

12. The high numerical aperture opto-mechanical scanner of claim 1, wherein said high numerical aperture opto-mechanical scanner further comprises a fiber coupling lens and an optical fiber disposed between said femtosecond laser and said scanning lens assembly.

13. The high numerical aperture opto-mechanical scanner of claim 1, wherein said moving carriage comprises at least one motor disposed on or in said moving carriage.

14. The high numerical aperture opto-mechanical scanner of claim 1, wherein said at least one motor comprises a voice coil.

15. The high numerical aperture opto-mechanical scanner of claim 1, wherein said moving carriage is a component of a flexure stage comprising a flexure which flexes substantially within said movable carriage x-y plane as said carriage moves along said fast scanning axis.

16. The high numerical aperture opto-mechanical scanner of claim 15, wherein said flexure stage comprises flexures disposed at opposite sides of said moving carriage.

17. The high numerical aperture opto-mechanical scanner of claim 15, wherein said flexure stage comprises a folded parallelogram flexure.

18. The high numerical aperture opto-mechanical scanner of claim 1, wherein said moving carriage comprises a linear stroke distance of more than about 5 mm.

19. A method for writing refractive index modifications using a high numerical aperture opto-mechanical scanner comprising the steps of:
    providing a fast axis scanner having a fast axis scanner comprising a moving carriage which defines a carriage x-y plane, said moving carriage movable in or parallel to said carriage x-y plane, along said fast scanning axis, an optical assembly with a NA greater than about 0.5 mechanically coupled to said fast axis scanner, a fast scanning motion axis of said optical assembly controlled by a waveform generator, a second motion axis orthogonal to said fast scanning motion axis, and a femtosecond laser to write said refractive index modifications;

providing a working surface comprising a surface of an optical material or a live animal or human eye; and writing by movement of said optical assembly along said fast scanning motion axis and said second motion axis at least a two dimensional refractive index modification of said material.

20. The method of claim 19, wherein said step of providing further comprises providing a third motion axis orthogonal to both of said fast scanning axis and said second motion axis, and said step of writing comprises writing a three dimensional refractive index modification of said material.

21. The method of claim 19, wherein said step of providing further comprises providing an optical modulator disposed between said femtosecond laser and said working surface, and said step of writing further comprises writing a three dimensional refractive index modification modulated by said optical modulator.

22. The method of claim 19, wherein said step of providing further comprises providing an optical modulator disposed between said femtosecond laser and said working surface or said second motion axis controlled by a stepping motion, and said step of writing comprises writing a microlens with a parabolic phase profile by use of intensity or speed control.

23. The method of claim 22 wherein said step of writing comprises writing an accumulated phase structure in modulo-$2\pi$.

24. The method of claim 23, wherein said step of providing further comprises providing an arbitrary waveform generator to control said fast scanning motion axis and said step of writing comprises writing a changing index profile controlled by a waveform of said arbitrary waveform generator along lines of said fast scanning motion axis.

25. The method of claim 19, wherein said step of providing said waveform generator comprises providing a sine wave generator and said step of writing comprises writing a negative refracting power lens.

26. The method of claim 19, wherein said step of writing comprises writing a positive refracting power lens using a two-scan process wherein each scan process of said two-scan process writes half a profile block.

27. The method of claim 19, wherein said step of writing comprises writing one or more arbitrary negative lenses or arbitrary positive lenses.

* * * * *